United States Patent
Lawlis et al.

(10) Patent No.: US 8,361,025 B2
(45) Date of Patent: Jan. 29, 2013

(54) PRESERVATIVE-FREE FOLLICLE STIMULATING HORMONE SOLUTION DELIVERY DEVICE

(75) Inventors: V. Bryan Lawlis, San Mateo, CA (US); Kirk J. Hayenga, San Mateo, CA (US); Darlene P. Horton, San Mateo, CA (US); Lucio Giambattista, East Hanover, NJ (US); David Desalvo, Florham Park, NJ (US); Antonio Bendek, Florham Park, NJ (US)

(73) Assignees: Carebay Holding Ltd., Tortola (VG); Itero Biopharmaceuticals, Inc., San Mateo, CA (US)

( * ) Notice: Subject to any disclaimer, the term of this patent is extended or adjusted under 35 U.S.C. 154(b) by 0 days.

(21) Appl. No.: 13/474,696

(22) Filed: May 17, 2012

(65) Prior Publication Data

US 2012/0265136 A1 Oct. 18, 2012

Related U.S. Application Data

(63) Continuation of application No. PCT/US2011/042972, filed on Jul. 5, 2011.

(60) Provisional application No. 61/361,319, filed on Jul. 2, 2010.

(51) Int. Cl.
*A61M 5/20* (2006.01)
*A61M 5/00* (2006.01)
*A61M 5/32* (2006.01)
*A61M 5/31* (2006.01)

(52) U.S. Cl. ........ 604/135; 604/198; 604/211; 604/232; 604/240

(58) Field of Classification Search ................ 604/131, 604/134, 135, 187, 197, 198, 206–211, 220, 604/218, 223, 224, 232, 240–242, 246
See application file for complete search history.

(56) References Cited

U.S. PATENT DOCUMENTS

| | | | |
|---|---|---|---|
| 5,728,074 A * | 3/1998 | Castellano et al. | 604/207 |
| 5,921,966 A | 7/1999 | Bendek | |
| 7,112,187 B2 * | 9/2006 | Karlsson | 604/187 |
| 7,195,616 B2 * | 3/2007 | Diller et al. | 604/224 |
| 7,427,275 B2 * | 9/2008 | DeRuntz et al. | 604/207 |
| 7,597,685 B2 | 10/2009 | Olson | |
| 8,062,255 B2 * | 11/2011 | Brunnberg et al. | 604/136 |

(Continued)

FOREIGN PATENT DOCUMENTS

WO 2009/150078 A1 12/2009
WO 2010/097125 A1 9/2010

(Continued)

OTHER PUBLICATIONS

The International Search Report, dated Feb. 29, 2012, for International Application No. PCT/US2011/042972, 3 pages.

(Continued)

*Primary Examiner* — Matthew F Desanto
(74) *Attorney, Agent, or Firm* — Kilpatrick Townsend & Stockton LLP

(57) ABSTRACT

A one-time use device to deliver preservative-free follicle stimulating hormone (FSH) solution is disclosed. The device includes a needle covered by a sliding needle shield, which covers the needle in all modes of the device. The device can be placed into a ready-to-use position in four or fewer user steps. The device has a knob for setting a desired dose of FSH. The knob includes longitudinally spaced elements respectively corresponding to the lock position and the seven or fewer discrete dosing positions. The device locks after one use and cannot be reused thereafter.

19 Claims, 18 Drawing Sheets

U.S. PATENT DOCUMENTS

| | | |
|---|---|---|
| 2003/0004467 A1* | 1/2003 | Musick et al. ................. 604/218 |
| 2004/0199117 A1 | 10/2004 | Giambattista |
| 2007/0233015 A1 | 10/2007 | Saiki |
| 2008/0147006 A1 | 6/2008 | Brunnberg |
| 2008/0154211 A1 | 6/2008 | Moller |
| 2009/0149809 A1* | 6/2009 | Bollenbach et al. .......... 604/111 |
| 2009/0308386 A1 | 12/2009 | Kronestedt |
| 2010/0305501 A1 | 12/2010 | Ratjen |
| 2011/0106008 A1 | 5/2011 | Kronestedt |
| 2011/0118667 A1* | 5/2011 | Zaiken et al. ................. 604/138 |

FOREIGN PATENT DOCUMENTS

| | | |
|---|---|---|
| WO | 2011/126439 A1 | 10/2011 |
| WO | 2011/145999 A1 | 11/2011 |

OTHER PUBLICATIONS

"Self-injecting with Gonal-f® RFF Pen—4 easy steps", 2008, 2 pages, EMD Serono, Inc., Rockland, Massachusetts, USA.

"Follistim® (follitropin beta injection) AQ Cartridge for use only with Follistim Pen®, Instructional Quick Guide", Dec. 2008, 2 pages, Schering Corporation, Kenilworth, NJ, USA.

* cited by examiner

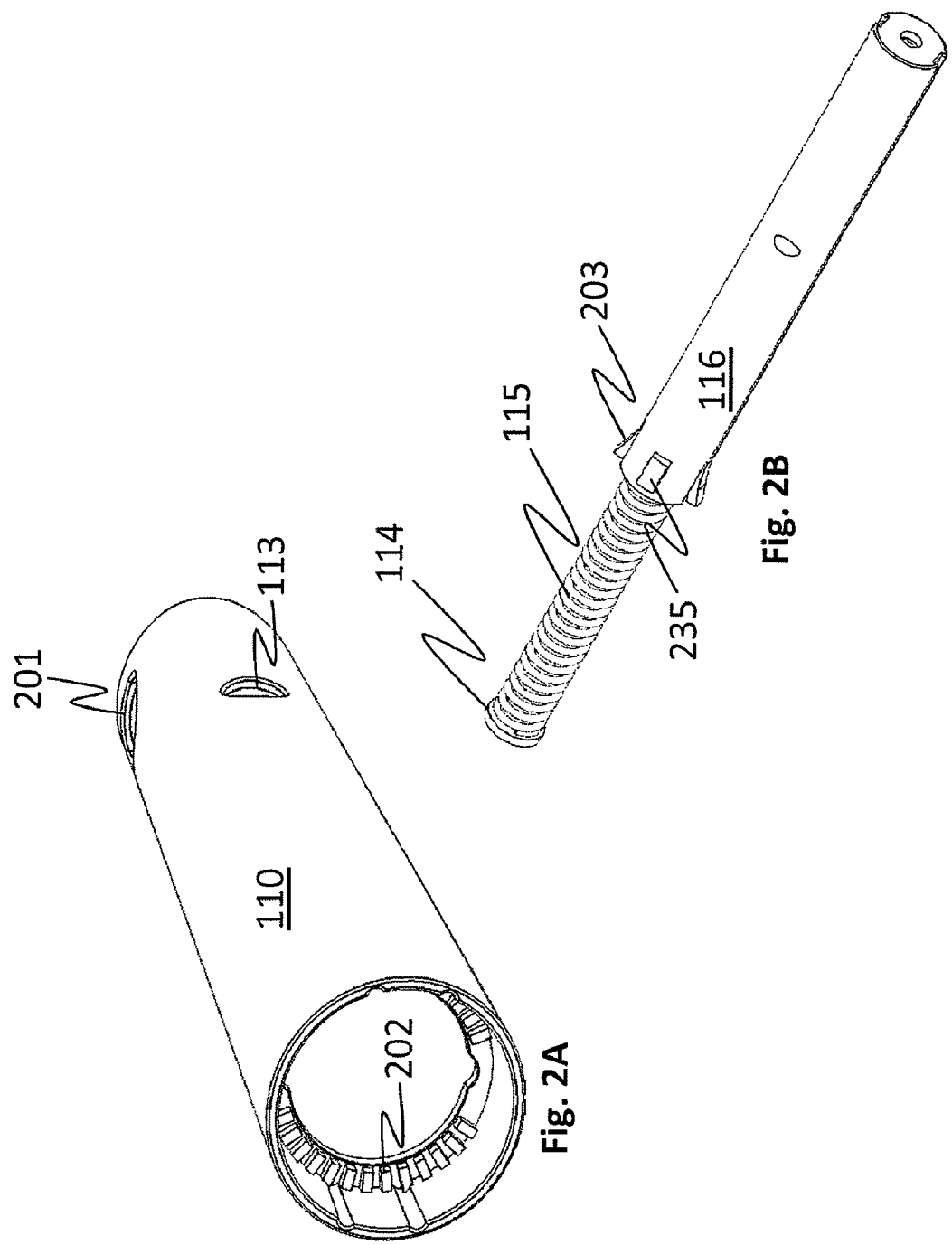

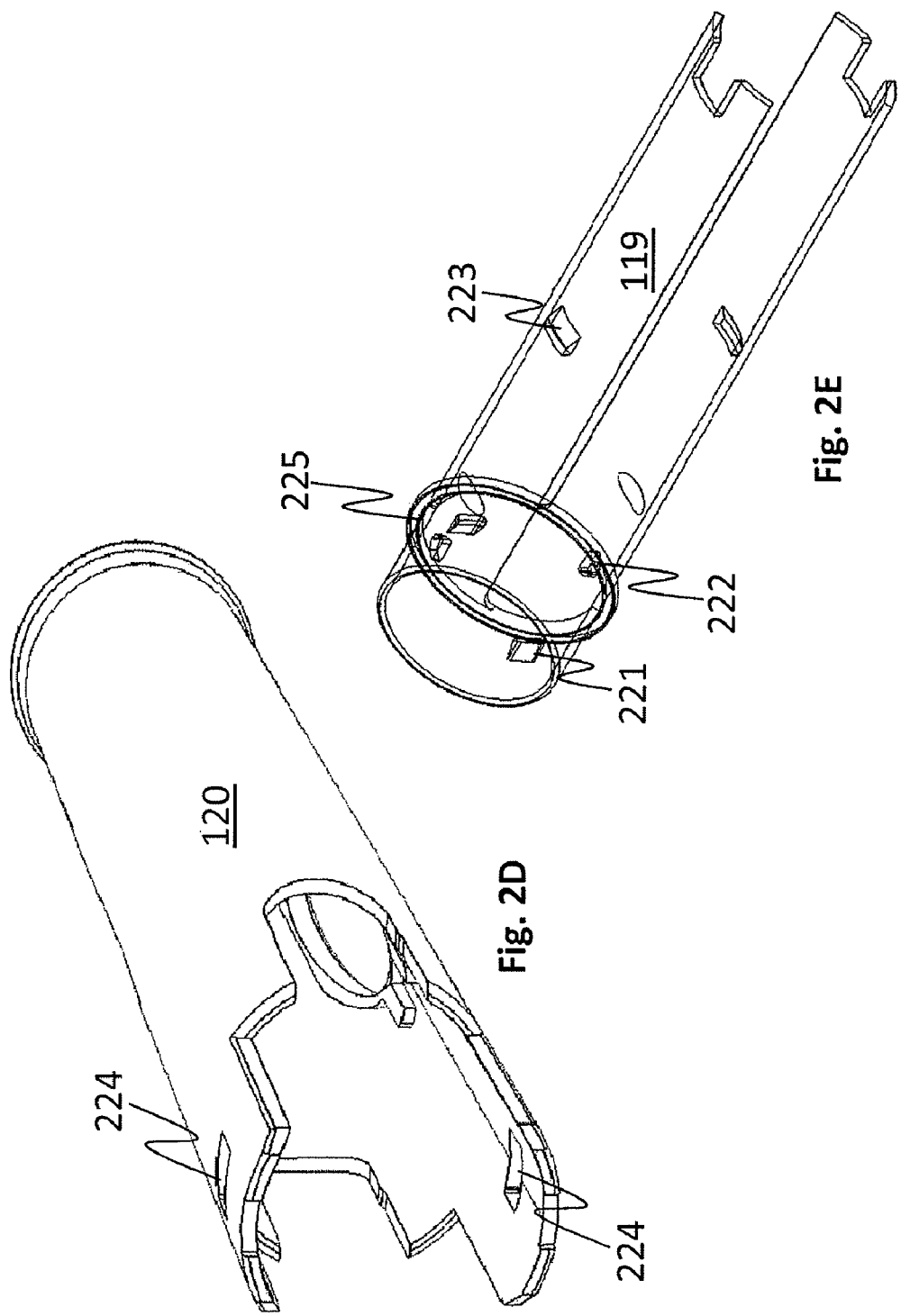

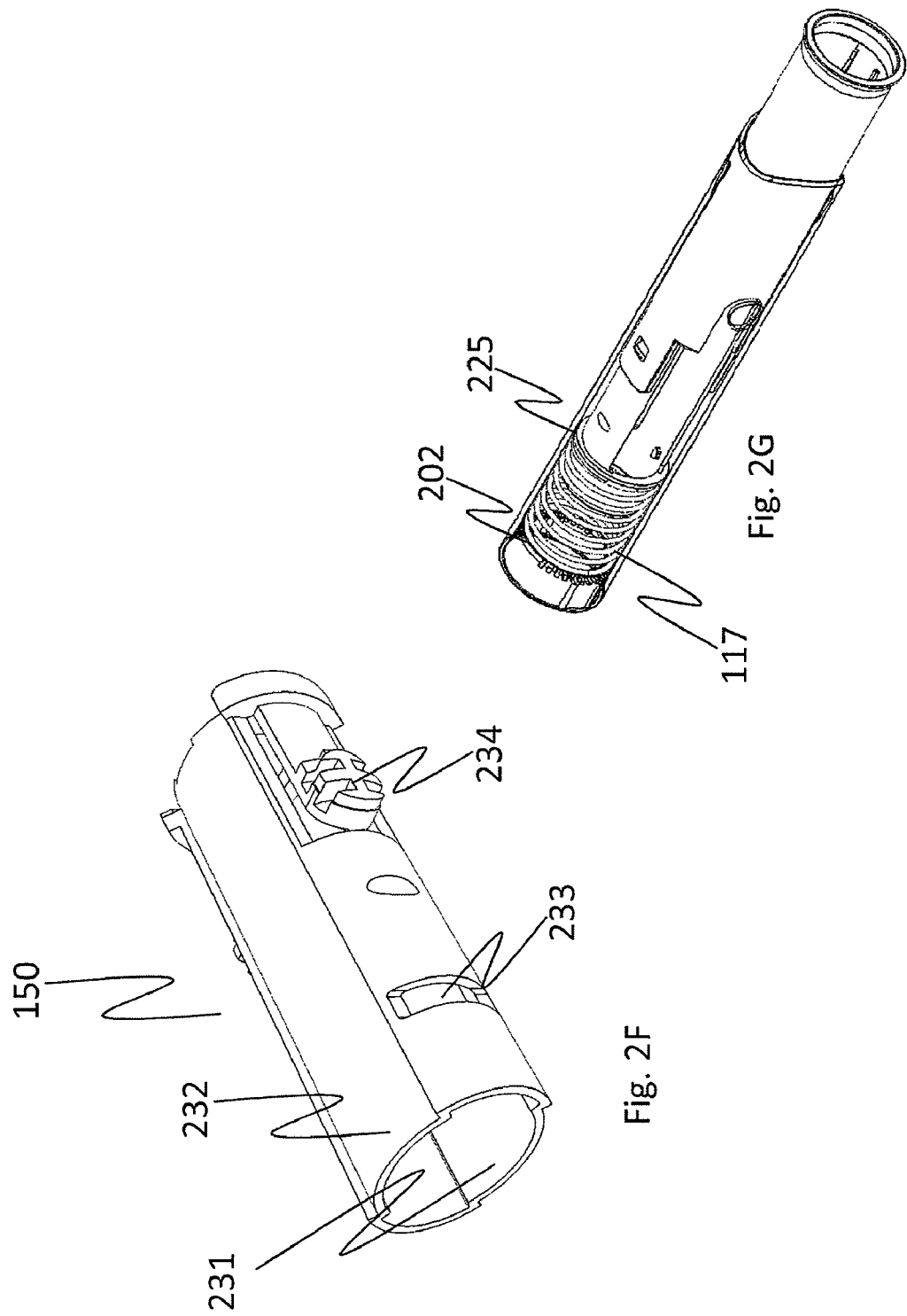

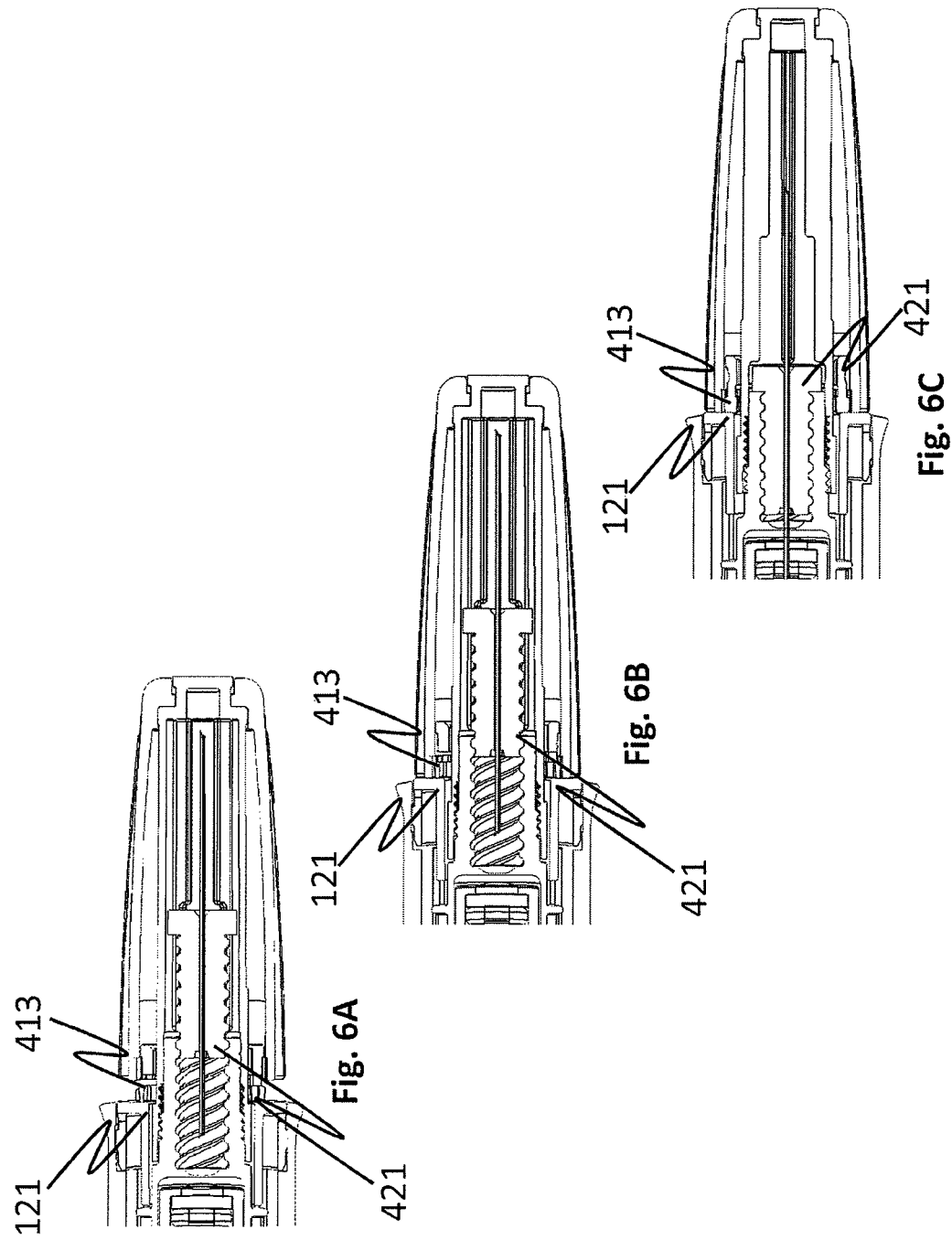

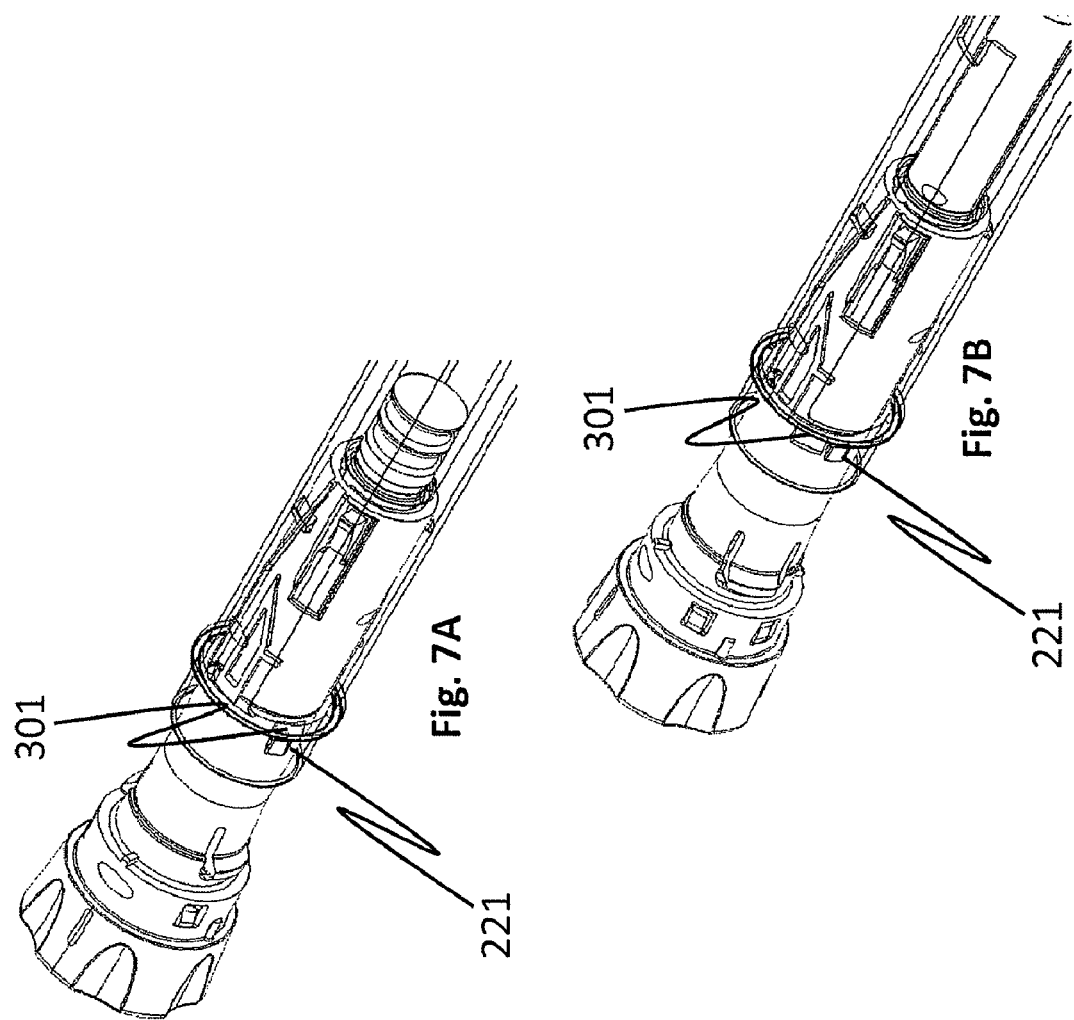

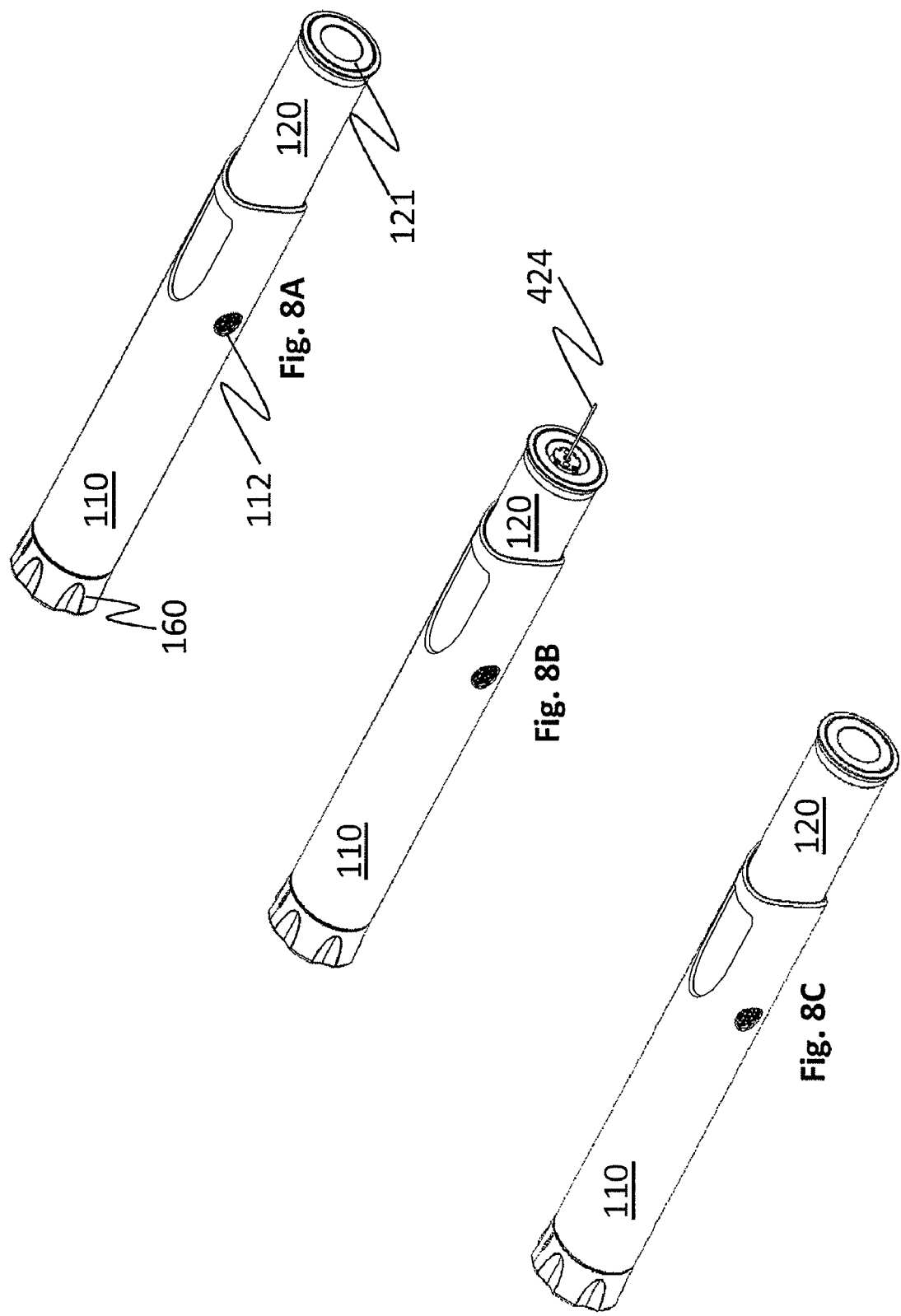

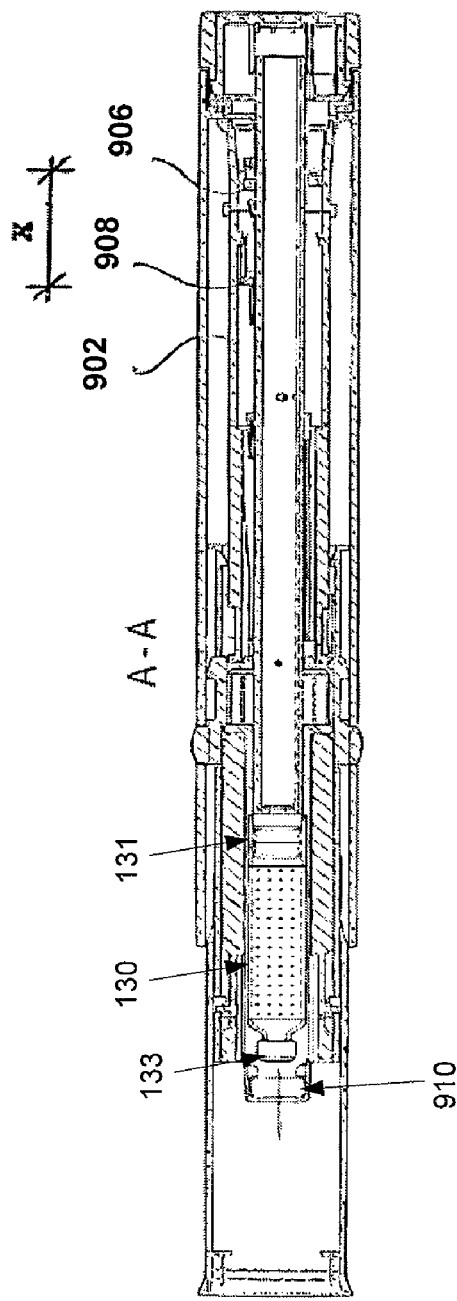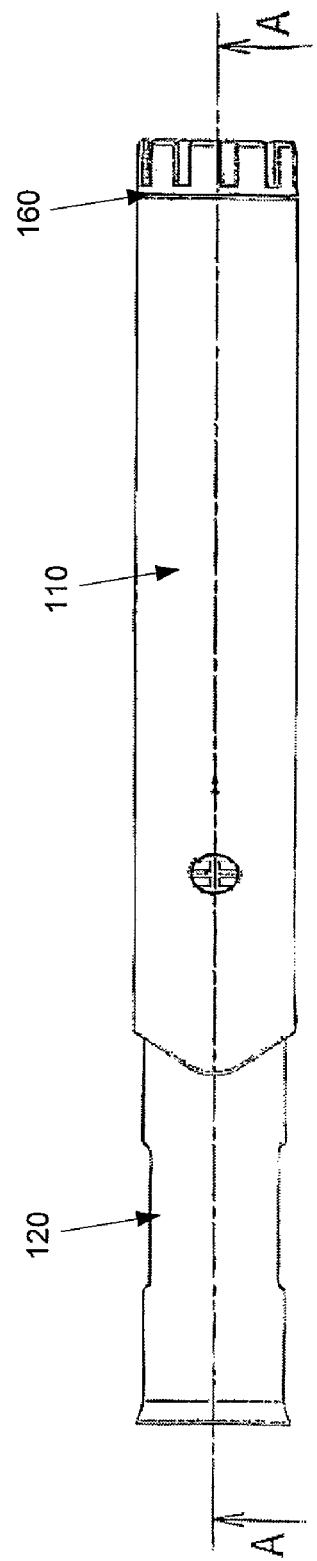
FIG. 9A

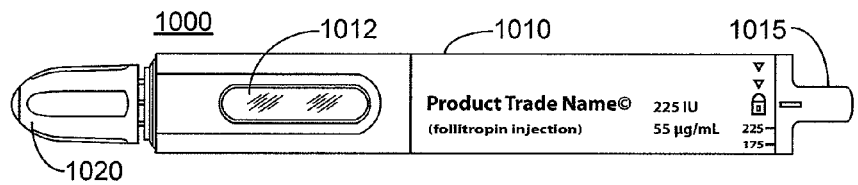
FIG. 10A
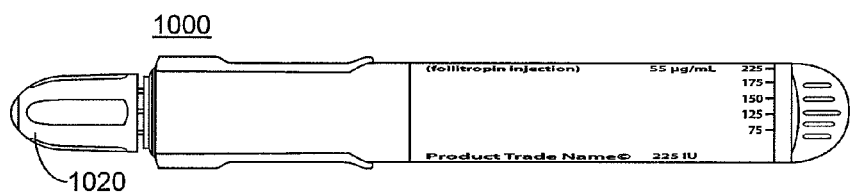
FIG. 10B
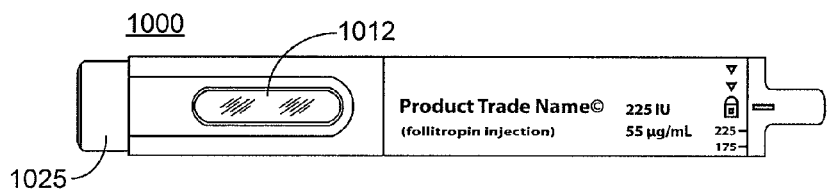
FIG. 10C
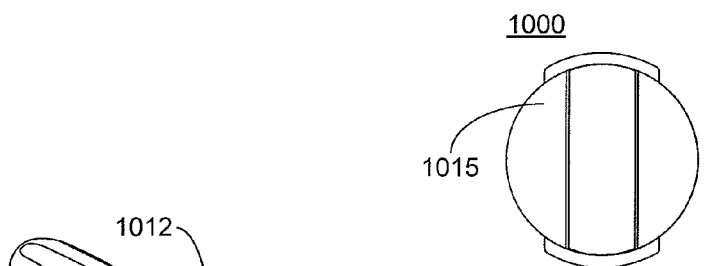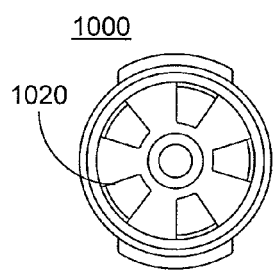
FIG. 10D    FIG. 10E
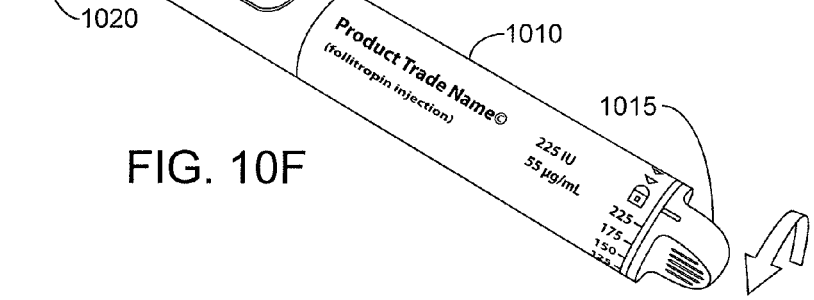
FIG. 10F

PRESERVATIVE-FREE FOLLICLE STIMULATING HORMONE SOLUTION DELIVERY DEVICE

This application is a continuation of International Application No. PCT/US2011/042972, filed Jul. 5, 2011, which claims the benefit U.S. Provisional Application No. 61/361,319, filed Jul. 2, 2010, the entireties of which are incorporated by reference herein.

BACKGROUND OF THE INVENTION

The invention is directed to a device for delivering follicle stimulating hormone solution, and more specifically to a one-time use and variable dosage, auto-injector device for self-injection of a preservative-free formulation of follicle stimulating hormone solution.

Follicle stimulating hormone solution (FSH) is used to treat infertility in women by stimulating one or more ovarian follicles (and the egg contained within the follicle) to develop and mature. FSH treatment is used when a woman desires pregnancy and her ovaries can produce a follicle but physiologic levels of FSH are not sufficient to make the follicle mature to ovulation necessary for a desired pregnancy. FSH treatment is also used to stimulate the development of multiple follicles and eggs for Assisted Reproductive Technology procedures (including in vitro fertilization) to achieve a desired pregnancy. Follicle stimulating hormone can also be used to treat infertility in men by increasing the production of sperm.

Self-administered treatment of FSH has been in existence for well over 10 years. Two well-known approved FSH formulations are EMD Serono, Inc.'s Gonal-f® and Merck & Co. Inc.'s Follistim®. Both products were approved in 1997 by the United States Food and Drug Administration (FDA) as lyophilized (or powder) formulations, requiring reconstitution with a diluent before injection. A typical FSH treatment plan requires one or two injections per day over a several-day period. For most patients, visiting a doctor's office for daily or twice-daily administration of FSH is completely impractical. Accordingly, the industry has supplied pen-like injection devices with liquid formulations of FSH that were approved in 2004 (Gonal-f RFF® pen and Follistim AQ® cartridge to be used with the Follistim Pen®), typically adapted from insulin injecting devices, for use by the patient to self-administer doses of FSH. These devices however include several deficiencies which add complexity to self-administration of FSH and the potential for needle or injection anxiety, dosing errors or lack of compliance.

These pens are remarkably difficult to use for the average person. Each prior art device requires several steps which, if not performed correctly and in the correct order, can result in a misadministration of FSH. Below are included examples of the required user steps for two pen injection devices supplied by industry leaders of self-administered FSH treatment.

| Gonal F ® RFF ("Gonal-F") Pen by Serono: | Follistim ® AQ Cartridge (follitropin beta injection)/Puregon ® ("Puregon") Pen by Merck: |
|---|---|
| 1. Examine the Gonal F pen to make sure the medication is clear | Remove the protective cap from the Puregon pen |
| 2. Remove the white pen cap | Unscrew the blue pen body from the yellow cartridge holder |
| 3. Wipe the threaded tip of the pen with an alcohol swab | Inspect the Puregon drug cartridge to make sure it is clear |
| 4. Remove the peel tab from the outer needle cap | Clean the rubber stopper of the Puregon drug cartridge with an alcohol pad |
| 5. Hold the outer needle cap firmly in one hand | Insert the Puregon cartridge into the yellow cartridge holder |
| 6. Press the threaded tip of the pen into the open end of the outer needle cap | Insert the blue pen body into the yellow cartridge holder with the black rod pressing against the rubber piston of the cartridge |
| 7. Twist the pen clockwise until the needle is securely attached | Screw the yellow cartridge holder toward the blue body making sure that the arrow on the cartridge holder points to the middle of the alignment mark on the cartridge body |
| 8. Remove the outer needle cap by pulling it straight off | Check that there is no gap between the yellow cartridge holder and the pen body |
| 9. To prime the pen for the first use, set the dose arrow to 37.5 | Clean the open end of the cartridge holder and the rubber stopper of the cartridge with an alcohol pad |
| 10. Pull out the white injection button as far as it will go | Remove the paper seal from the BD Ultra Fine Pen Needle Unit |
| 11. Remove the inner needle cap | Push the end of the yellow cartridge holder into the outer needle shield and screw on tightly |
| 12. Hold the pen so the needle points upward | Use an alcohol pad to clean the area where the needle will be inserted |
| 13. Gently tap the pre-filled reservoir with your finger to let any air bubbles rise to the top | Remove the outer needle shield leaving the inner needle shield in position |
| 14. Push in the white injection button and hold until you hear a click | Remove the inner needle shield |
| 15. A small amount of liquid should appear from the needle tip which means the pen is now primed and ready for use | Hold the pen with the needle pointing upward and tap the cartridge holder gently with your finger to help the air bubbles rise to the top of the cartridge |

| Gonal F ® RFF ("Gonal-F") Pen by Serono: | Follistim ® AQ Cartridge (follitropin beta injection)/Puregon ® ("Puregon") Pen by Merck: |
|---|---|
| 16. Replace the inner needle cap | At this point, you should see a droplet forming at the top of the needle |
| 17. To set the dose, turn the dosage dial so your prescribed dose lines up with the prescribed dose arrow | If you do not see a droplet, dial the dosage knob one mark on the dosage scale until you hear a click |
| 18. Load the dose by pulling out the injection button as far as it will go | With the needle pointing upward, push the orange injection button in all the way and then check the needle to make sure the drop of fluid comes out |
| 19. Confirm the correct dose by looking at the last fully visible red flat arrow on the injection button which indicates the dose that is loaded and ready to be injected | Turn the dosage knob until the desired dose is in the middle of the dosage window |
| 20. Clean the recommended injection site with an alcohol swab | Pinch up a large area of the cleansed skin between your finger and thumb |
| 21. Remove the inner needle cap | With your other hand, insert the needle directly into the skin at a 90-degree angle |
| 22. Hold the pen in one hand and with the other hand pinch the skin around the injection site | Fully press the end of the orange injection button and wait five seconds before removing the needle from the skin |
| 23. To inject, insert the needle into the skin at a 90-degree angle | Place the outer needle shield on the table with the opening pointing up |
| 24. Once the needle is inserted, release the pinched skin and push the injection button until it stops clicking | Insert the needle attached to the Puregon pen into the opening of the outer needle shield and push down firmly |
| 25. Keep the needle in the skin for at least five seconds and then remove the needle | Grip the outer needle shield and use it to unscrew the needle |
| 26. Hold the pen firmly by the clear drug reservoir to recap the needle with the outer needle shield to avoid needle pricking and replace the outer needle cap | Place the needle with the outer needle shield in the Sharps container |
| 27. Grip the outer needle cap firmly and unscrew the pen from the needle by turning counterclockwise | Put the blue cap back on the Puregon pen |
| 28. Dispose of the used needle in a Sharps container | Store the pen and cartridge for the next dose |
| 29. Recap the pen | |

Gonal-f currently holds approximately 53% share of the market (EU, North America, & Japan), while Follistim® (also known as Puregon® outside of the US) holds approximately 47%. The producers of the corresponding pens for these products directly compete with one another, but have yet to improve these devices beyond the complex steps noted above. The complexity of self-administration of needles has been identified in published papers as a problem with FSH treatment. While the currently marketed pens may offer less complexity over a simple needle, syringe, and vial, they still have not fully addressed the needs of the patient population. One of the pens is a rebranded pen originally intended for use with insulin injections. Accordingly, the dosing markings on the pen have no specific relationship to the doses required for FSH injections, and must be interpreted accordingly. The dose increments available are extremely small and bear no relationship to commonly used doses of FSH. For example, the Follistim Pen® has 54 dose settings available. This is because this pen is actually a rebranded insulin pen in which each dose increment corresponds to 1 international unit (IU) of insulin. Accordingly, only very few dose settings (approximately 10%) of the available doses are used. This only adds to user confusion and the tendency to commit dosing errors.

The existing FSH pens are designed as multi-use pens. One available pen is supplied with a specified quantity of protein as measured in IUs that is typically more than what is needed for a single administration. Another available pen requires assembly with a multi-use cartridge that typically contains more IUs of the protein than what is required for a single administration. The advantage of a multi-use pen is that a patient can use the same pen for more than one dose, lessening some of the complex steps involved for a subsequent injection with the same pen. However, one pen or cartridge is not sufficient to complete one treatment cycle, requiring a patient to use at least 2-3 pens or cartridges and as many as 14 pens or cartridges to complete their treatment cycle. The total number of pens or cartridges to be used cannot be predicted before treatment because the daily dose and the total number of days to complete a course of therapy vary according to the patient's clinical response. This often leads to waste of the remaining medication in one or more pens or cartridges or the need to give 2 separate injections to administer one dose. Accordingly, a patient must implement a dosing routine which works around the available amount of FSH solution from their prescribed pens or cartridges. The patient must also be responsible for calculating the difference between the total dose contained in a pen or cartridge minus the last doses administered from that pen or cartridge and the current dose in order to make sure that the pen or cartridge that the patient is currently using has enough FSH solution to provide the needed dose. For chronic conditions such as diabetes, this approach may be appropriate because the patient has many months to years to develop the technique for proper dose selection and use of the pens. However, for a 9-14 day treatment cycle for treatment of infertility in healthy women attempting to get pregnant, the existing options are far more complex than they need to be.

Complexity of use is not the only long-felt problem which has not been addressed by the industry. The use of a needle in general can trigger a mental condition that is known as needle or injection anxiety. Simple viewing and handling of a needle can cause many patients to experience symptoms of anxiety or an enhanced physiologic response that results in nausea, lightheadedness, and fainting and may trigger an enhanced painful response. In addition, the need for the patient to manually depress the plunger rod of these pen-injectors is a reminder to the patient that the patient is injecting himself or herself with medication adding to the potential anxiety. Some patients will simply not seek out the therapy due to their fear of or anxiety with needles and injections. Others will have their partners administer to them the injection. Needle and injection anxiety can accordingly result in a general discomfort and fear which leads to undue stress, needle stick accidents, lack of compliance, lightheadedness or fainting, and lack of seeking treatment.

Further, many of the pens or cartridges utilize formulations of FSH which are intended to be saved for multiple uses. This requires formulations which include preservatives, such as benzyl alcohol or m-cresol. The side effect of this, however, can be a painful sensation caused by the injection of the preservative into the patient. This is often described as a burning-like sensation, separate from the pain induced by the needle prick alone. In addition, benzyl alcohol has been associated with significant side effects such as kernicterus and death in newborn babies.

It is clear that there have been long-felt needs which have not been addressed by industry leaders to solve the problems noted above. The problems shown above are not merely separate and distinct, but are interwoven, complex and tangled. Complexity of use is notably a derivative of implementing a reusable pen, or a reusable pen in combination with a reusable FSH cartridge, which requires a new needle for each use. Further, needle or injection anxiety is induced by the need to directly handle and visualize a needle for a reusable pen as well as the need to manually depress the plunger rod. However, needle anxiety cannot be addressed by the current pens, as these pens are required to be reused, and thus require a new needle to be attached and handled for each use. Painful burning sensations induced by preservatives in FSH solutions are also not addressable by the prior art pens because the FSH cartridges need to be used over many treatments. Thus, the use of a preservative in a liquid formulation is necessary to minimize or prevent bacterial overgrowth of the remaining liquid in the pen or cartridge.

All of the noted problems raise safety concerns and may lower the efficacy of the FSH treatment, but also are seen as individual solutions in their own right, which further complicates identification of the issues. The preservatives used in the FSH solutions are seen as beneficial in one aspect because the pens or cartridges can be used multiple times. Further, the pens currently implemented are compatible with syringes and cartridges used with other medical conditions (e.g., insulin cartridges for diabetes) which reduces costs. Thus, one problem enhances or causes another, but is valued in some aspects to address a separate issue. Some of these issues are seen to lower costs, but as the safety issues rise, the detriment to the patient and greater society in bearing these costs is enhanced.

Thus, identification of the problematic issues of self-administration of FSH is complex in that currently implemented features are perceived solutions that actually present further problems in their own right. Accordingly, there is a tendency in the industry to hold on to these features. It would be beneficial to have a device which addresses these issues, while concurrently not detracting from the benefits of the prior art pens. Embodiments of the invention address these and other issues.

BRIEF SUMMARY OF THE INVENTION

One embodiment of the invention provides a single-use auto-injection device for self-delivery of follicle stimulating hormone solution. The device includes an elongated main housing with distal and proximal portions arranged along a longitudinal axis. An elongated rotator is connected to the proximal portion of the main housing and rotatable about the longitudinal axis with respect to the main housing. A knob extends from the proximal portion of the housing and is rotatable with respect to the main housing between a lock position and seven or fewer discrete dosing positions for setting variable dose delivery of follicle stimulating hormone (FSH) solution. The knob has longitudinally spaced elements respectively corresponding to the lock position and the seven or fewer discrete dosing positions. A plunger rod is rotatably engaged to a portion of the rotator and longitudinally spring biased. The plunger rod is rotatably locked to the knob in the locked position on the element corresponding to the lock position. The plunger rod is incrementally movable along the longitudinal axis between the element corresponding to the lock position and one of the elements of the seven or fewer discrete dosing positions. A permanently encased needle assembly has a permanently attached needle. The needle has an internal end and a working end. A cartridge holder is proximately attached to the needle assembly. The cartridge holder holds an elongated drug cartridge containing the FSH solution. The FSH solution is sterile and preservative free to allow only a single use of the device. The drug cartridge is permanently encased within the cartridge holder and has a penetrable membrane or disc as it is referred to in ISO 11608-3:2000 adjacent the internal end of the needle and a movable plunger distal to and adjacent to the plunger rod. The drug cartridge is fluidly disconnected from the internal end of the needle when the knob is in the locked position. A needle shield is movable with respect to the main housing along the longitudinal axis between a covering position that is distal to the working end of the needle and an injecting position that is proximal to the working end of the needle. The needle shield is spring biased to be normally placed in the covering position and opaque to substantially block user view of the working end of the needle in the covering position. The needle shield has a cam or follower which rotatably and longitudinally interfaces with a respective follower or cam of the rotator during a compression stroke of the needle shield from the covering position to the injecting position. A removable cap is positioned distal to the end of the needle shield to cover the working end of the needle contained within the needle assembly. The needle assembly or the drug cartridge is movable along the longitudinal axis to a priming position via engagement with the cap or plunger rod, respectively, to cause the internal end of the needle to penetrate the membrane and fluidly connect with the drug cartridge to prime the needle with the FSH solution. During the compression stroke, the needle shield moves to the injecting position and rotates the rotator to rotatably engage the plunger rod and cause the plunger rod to move to one of the elements of the seven or fewer discrete dosing positions and compress the movable plunger to auto-inject or deliver a corresponding discrete dose amount of FSH solution from the working end of the needle. The device-specific user steps needed to place the unpackaged device from the lock position to a ready-to-use position are four or fewer.

In one aspect of the device, the knob is rotatable with respect to the main housing between the lock position and a prime position.

In another aspect of the device, the knob includes a longitudinally spaced priming element corresponding to the prime position, the priming element being located between the lock position and the seven or fewer discrete dosing positions.

In another aspect of the device, rotating the knob to or past the prime position rotates the plunger rod from the lock position and incrementally moves the plunger rod along the longitudinal axis between the element corresponding to the lock position and the priming element.

In another aspect of the device, the plunger rod is incrementally moved along the longitudinal axis to move the drug cartridge into the needle assembly and cause the membrane to be punctured by the internal end of the needle and prime the needle with the FSH solution.

In another aspect of the device, the user steps needed to place the unpackaged device from the lock position to the ready-to-use position consist of priming the needle with the FSH solution by rotating the knob from the lock position, past the priming position, to one of the seven or fewer discrete dosing positions, and removing the needle cap.

In another aspect of the device, distal movement of the main housing with respect to the needle shield held against relatively immobile tissue causes the compression stroke and auto-injection of the FSH solution.

In another aspect of the device, the rotator knob is visually marked with discrete positions indicating the seven or fewer discrete dosing positions.

In another aspect of the device, the priming position is not marked on the knob.

In another aspect of the device, the needle assembly includes a hub attached to the needle, the hub being threadably engaged with a cartridge holder member of the needle assembly.

In another aspect of the device, the removable cap is rotatably engaged with the cartridge holder member, and rotation of the removable cap disengages the removable cap from the device and also moves the hub in a proximal direction with respect to the cartridge holder member and accordingly causes the membrane to be punctured by the internal end of the needle and prime the needle with the FSH solution.

In another aspect of the device, the user steps needed to place the unpackaged device from the lock position to the ready-to-use position consist of priming the needle with the FSH solution by removing the needle cap and rotating the knob from the lock position to one of the seven or fewer discrete dosing positions.

In another aspect of the device, the needle shield includes a locking element which locks to the rotator or main housing during a decompression stroke of the needle shield from the injecting position to a recovering position to recover the working end of the needle, and the needle shield is immovable with respect to the main housing after moving to the recovering position.

In another aspect of the device, the plunger rod contacts one of the elements of the seven or fewer discrete dosing positions with enough force to cause an audible click to be heard by the user.

In another aspect of the device, the drug cartridge is 1.5 ml in volume.

In another aspect of the device, the plunger rod is configured to deliver a maximum dose of the FSH solution within five seconds after the needle shield is placed in the injecting position.

In another aspect of the device, the FSH solution does not contain a preservative such as benzyl alcohol or m-cresol In another aspect of the device, the needle shield completely blocks the user's view of the working end of the needle throughout the duration of the injection from when the needle shield is in the covering position when the distal end of the needle shield is held against the user's tissue before and after the compression stroke occurs.

These and other embodiments of the invention are described in further detail below, which provides an exemplary implementation of the embodiments and aspects disclosed herein.

BRIEF DESCRIPTION OF THE DRAWINGS

FIG. 2A is a perspective view of a tubular housing of the device of FIG. 1A.

FIG. 2B is a perspective view of a plunger rod assembly of the device of FIG. 1A.

FIGS. 2D and 2E are perspective views of an actuator of the device of FIG. 1A.

FIG. 2F is a perspective detail view of a medicament container holder of the device of FIG. 1A.

FIG. 2G is a detail perspective view of the device of FIG. 1A in a locked state.

FIGS. 6A-6C are cross-sectional side views of the cap/priming assembly of FIG. 4A in various stages of operation.

FIGS. 7A and 7B are perspective views of the dosing knob of FIG. 3A in locked and unlocked states, respectively.

FIGS. 8A-8C illustrate, in perspective, the medicament delivery device in different operating modes.

FIG. 9A shows side and cross-sectional views of an FSH delivery device according to an embodiment of the invention.

FIGS. 10A and 10B are different side views of a tubular FSH delivery device, according to an embodiment of the invention.

FIG. 10C is a side view the FSH delivery device of FIG. 10A in a mode of operation.

FIGS. 10D and 10E are distal and proximal views, respectively, of the FSH delivery device of FIG. 10A.

FIG. 10F is a perspective view the FSH delivery device of FIG. 10A in a mode of operation.

DETAILED DESCRIPTION OF THE INVENTION

Figure 1A:
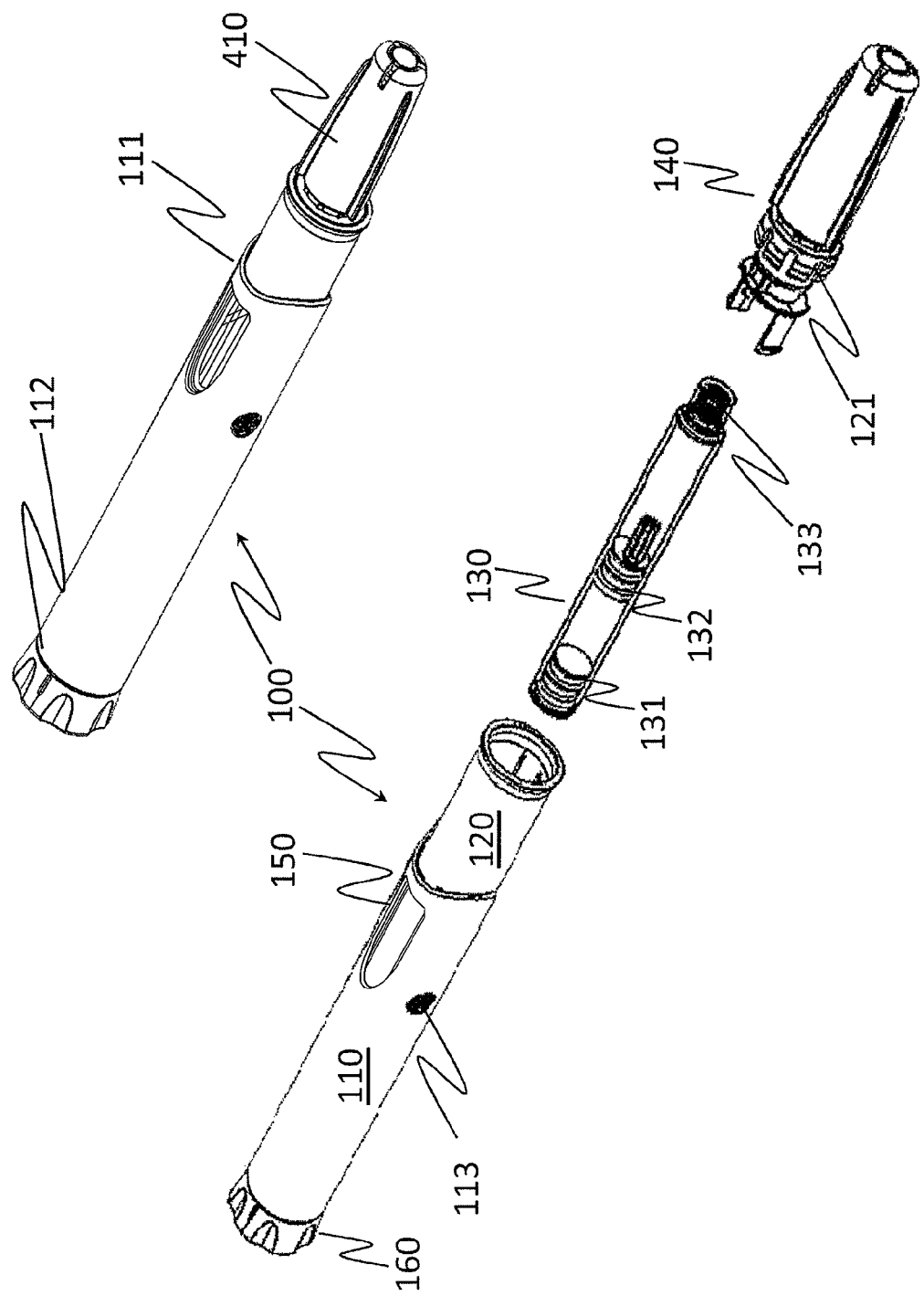
FIG. 1A is a perspective view of an FSH delivery device according to an embodiment of the invention.

Embodiments of the invention address the deficiencies of the prior art by providing a easy-to-use auto-injection device for which the number of device-specific user steps needed to place an unpackaged FSH solution delivery device from a locked position (as unpackaged) to a ready-to-use position is four or fewer, or consists of two or three steps exactly in some embodiments. Further, the total number of steps required to fully use the device is only nine, including disposal. The exemplary steps are as follows:

1. Examine the device to make sure the medication is clear
2. Hold the device vertically with the needle cap up and the dosing knob down. Remove the cap from the end of the device (which may prime the device in some embodiments)
3. Dial in correct dose (which may prime the device in some embodiments)
4. Prepare the injection site by cleansing the injection site with an alcohol swab
5. Hold device on injection site at a 90-degree angle to the skin
6. Push down device onto skin, which will push the needle shield into the device, allowing the needle to penetrate into skin and for the device to automatically inject drug into the body. In some embodiments, the device will create an audible click when the device starts injecting the medication.
7. Hold in place for five seconds until an audible click (some embodiments) is heard indicating the full dose has been injected into the body
8. Remove the device from the skin, which will cause the needle shield to cover the needle and to lock in place thus avoiding post-injection needle sticks
9. Dispose of device as directed by a physician This list of user steps shows that the device disclosed herein is much less complex to use than the prior art pens described above. As the complexity of use for the device is relatively low, the device addresses the ease-of-use issues associated with use of the prior art pens. Here, the device can be used within nine easy-to-follow steps, as opposed to the approximately 30 steps required for the prior art pens.

Further, after unpacking the device, it can be set to a ready-to-use state within four or fewer steps, or exactly two in some embodiments. It should be understood that these steps regard user performed mechanical inputs to settings on the device (e.g., knobs) and/or user removal of components (e.g., tip cover) to change the device from a safe and unusable setting (e.g., non-moveable, locked, and unprimed) to a ready-to-use setting (e.g. moveable, unlocked, and primed). As compared to the prior art pens, most notably absent is the need to handle, or even view, a needle, to load a drug cartridge, and to manually push the plunger rod as these steps are eliminated by the delivery device disclosed herein.

The device disclosed herein is a one-time use FSH delivery device which supplies a preservative-free formulation of FSH solution, and accordingly prevents any potential side effects of the preservative. The preservatives added to the available preparations of FSH are not part of the active pharmaceutical ingredient and are added to formulations to minimize bacterial growth and to enable the products to be sold as multi-use devices. However, both benzyl alcohol and m-cresol have been associated with pain on injection. And worse side effects such as kernicterus and neonatal death have also been reported for benzyl alcohol. Yet the field of infertility expects FSH formulations to be used in a device to have a preservative because the only devices available for FSH are multi-use devices. Thus this single use device with a preservative-free formulation is out of the norm established by the industry, as the FSH solution is sterile before use, and the device is unusable after one use.

At no point in using the device is the user required to handle or directly view the needle which injects the FSH solution. The view of the needle when looking at the device from the side is completely blocked by an opaque needle shield before use, and during use, as the shield moves into the main housing of the device while the needle is moved into the skin for injection. Externally, all that appears is a cylinder being compressed against the user. This arrangement can prevent or significantly lessen inducement of needle anxiety by blocking the user's view of the needle, and also blocks views of the needle in public. This arrangement requires the use of a pre-assembled and one-time use device, as the patient must be prevented from handling and viewing the needle for this feature to have affect. Again, this is out of the norm established by the industry which promotes reusable devices, and the needle handling which must accompany them.

At no point during use of the device does the patient have to manually push on a plunger rod to self-inject the medication. The "auto-injection" feature of the device leads to automatic injection of the FSH solution through the patient's skin when the patient presses the devices against the skin far enough to activate the auto-injection features. This feature helps to prevent or lessen injection anxiety because the patient does not have to worry that they have not injected all of the medication by not pushing down the plunger rod sufficiently. This feature also can help remove the sense of directly injecting via the user's continual physical input to the device and the injection of the FSH solution, which can add to anxiety, by removing the user's control over the delivered rate of injection.

Generally, a self injection by non-medical personnel, such as a therapy receiving user of the device, also leads to a comparatively longer rate of injection as the untrained individual is more likely to take their time to make sure that the injection is completed correctly, however this is often to an overzealous and unnecessary degree. Combined, the patient is more conscious of the injection which may cause more discomfort or anxiety to the patient. With the device, the needle is not visible and the user is primarily conscious of only compressing a spring loaded telescoping tube against their skin, with injection occurring from a secondary mechanical actuation that is initiated by the compressing motion. The rate of injection is determined from a mechanical release or transfer of a stored energy, such as the release of a spring, and not by the user's continual input to a syringe. Thus, the sense of directly injecting the FSH solution can be alleviated in many cases.

The preservative-free FSH solution is supplied in 1.5 ml cartridges specifically for use with the device, and the cartridges are permanently encased within the device reducing the required assembly steps for the patient. The device also becomes permanently locked after one use, to prevent any inclination to reuse the preservative-free FSH solution.

The device may be available in varying maximum dosing amounts that represent the most common initial doses used for FSH based on robust research of medical chart reviews in the US and Europe. The up to 6 fewer than maximum dose settings on each device have also been selected to be generally aligned with what a physician will use when decreasing the dose from the initial higher dose. The intended use of the device is that the patient will only use one device for each injection and that the entire dose of the FSH solution present within the device (i.e., the maximum setting) will be injected in the great majority of cases.

Generally, the up to 6 fewer than maximum dose settings (i.e., the available doses lower than the maximum setting) are included on the device so that the patient may use an available and in-possession device contemporaneously (e.g., on that same day) with when their physician chooses to decrease the dose. Accordingly, the adjustability of the device prevents the need to have to purchase a new device with a prescription change. On subsequent days, a comparatively lower maximum dose (i.e., lower than an initial dose over an intended therapy schedule) device will be available so that the patient can use the lower dose device. For example, a user may be in possession of a device having a maximum available dose of 225 IU of FSH solution and the user's doctor changes the dose prescription to 150 IU of FSH solution. Accordingly, the user can set the device to lower the delivered dose and account for the contemporaneous dose change. The next day, the user may obtain a device having a maximum available dose of 150 IU of FSH solution.

The availability of different maximum dosage devices provides an advantage for the patient in that the cost of the medication at the lower dose will be lower and there will be far less probability of wasting unused drug. It should be understood that the cost of the FSH solution currently accounts for almost 100% of consumer/retail cost for all available FSH delivery devices. The availability of varying maximum dosages allows the device to require only 7 or fewer dose settings, as opposed to the large multitudes of dosage settings required by the prior art pens. These dosing options simplify dosing and aid in ease of use, as the user in almost all cases needs only set the device to the maximum dose setting.

Dosing for the device is set by the user by turning an adjustable knob with seven or fewer positions, which relate to seven or fewer dose amounts, respectively. The doses are typical doses used for FSH and are preset with indicated simple labeling (e.g. 1, 2, 3, 4, 5, 6, etc.) and do not need to be interpreted, correlated or calculated by the user. As the device is solely intended for FSH delivery, there are no unusable and available dosing levels, as there may be for the prior art pens which are adapted from non-FSH industries. This greatly lowers user confusion by reducing the complexity of setting the dose level. Accordingly, the user simply has to set the dial and use the device.

As noted above, the user also does not have to insert a new FSH cartridge to use the device. By using a customized preservative-free FSH cartridge in a 1.5 ml size, the device is not limited to commonly available "off-the-shelf" volumes of preservative containing FSH formulations. The customized device will be available in doses that are most commonly prescribed for the treatment of infertility. This ultimately reduces user steps by preventing the need to reload the device, and can accordingly provide a dosing schedule which is uncomplicated to follow, as the device can simply be set, used and disposed of. These advantages are borne out by the preservative-free FSH solution contained within the permanently encased cartridge, which prevents reuse of the device.

All of these features combined result in a device with greater efficacy of use than the prior art pens, and result in a more successful FSH treatment. A one-time use device is contrary to the industry standard reusable pen, which reuses devices and drug cartridges. However, the inability to predict the total dose required for a given treatment cycle and the few available doses of the existing pens and cartridges make it nearly impossible to avoid waste of medication adding to the cost of the therapy since the unused medication cannot be returned to the pharmacy. The current invention reduces costs overall by increasing efficacy of use, reducing dosing errors, and minimizing drug waste.

Accordingly, the problems with the prior art are fully addressed by the embodiments of the invention by providing a relatively simple-to-use device with fewer required steps. It should be understood that references made to FSH within the following disclosure are intended to refer to a sterile and preservative-free solution of FSH. A preservative-free solution of FSH is a solution that would be supportive of microbial growth sufficient to render the drug product unsafe for human use if not for the sterile conditions. Such preservative-free solutions do not contain pharmaceutically acceptable antimicrobial agents that are suitable for injection into humans such as benzyl alcohol or m-cresol. A preservative-free solution of FSH would not pass the pharmaceutical industry's standard Antimicrobial Effectiveness Test, otherwise known as the Preservative Challenge Method, described in US Pharmacopoeia <51>, which demonstrates the antimicrobial effectiveness of a preservative system. The acceptance criteria for antimicrobial effectiveness is described in detail in USP <51>, but in general, a formulation free of an antimicrobial preservative would fail the test by failing to demonstrate a 1 to 3 log reduction in bacteria counts, or an increase in yeast and mold counts, from the initial level within one to two weeks.

FSH is available through commercial sources. Typical concentration in injection pens deliver between 600 and 833 IUs per ml of solution. Available doses of one commercialized product are 300 IU, 450 IU, and 900 IU. Available doses with the other commercialized product are 150 IU, 300 IU, 600 IU, and 900 IU. Typical doses per injection range from between 75 IU to 225 IU for one of the female infertility indications and 150 to 450 IU for the other, with a few doses in between for each indication. Thus no set of available doses for any single commercialized product is customized to its potential use for the treatment of infertility.

The device generally includes a tubular-shaped main housing which is elongated along a longitudinal axis. The main housing is what the patient will grip during use of the device. A tubular needle shield extends from a distal end of the main housing. The needle shield telescopes into the main housing and is spring loaded to normally assume an extended covering position over a needle. In some embodiments, the needle shield is locked in the extended position until the dosing knob is turned to select a dose at which time the needle is primed and the needle shield is unlocked. A removable cap is located at the distal end of the needle shield. Once the cap is removed and the needle shield is unlocked by selecting a dose the needle shield can telescope into the main housing via a compression stroke to assume an injecting position to enable the needle to penetrate the skin. The needle shield is opaque and substantially blocks user view of the needle in the covering position and in the injecting position during use. Once the compression stroke is completed and the device and needle are pulled away from the skin, the needle shield assumes the extended position and is locked in place so that the device and single-use Cartridge cannot be used again. This also prevents accidental needle sticks since the used needle is once again hidden by the needle shield. The main housing and needle shield appear together as an elongated tube. A removable cap is located at the distal end of the needle shield.

A knob extends from a proximal end of the main housing. The knob is rotatable from an initial lock position to a plurality of discrete dose settings for a sterile and preservative-free FSH solution, generally seven or fewer. The knob is visually marked accordingly to the seven or fewer doses with rotational reference to the main housing, and in some embodiments with a prime/unlock position. An elongated internal portion of the knob extends into the main housing and locks with the needle shield in the lock position. Turning the knob from the locked position accordingly unlocks the needle shield. The internal portion of the knob also interfaces with a rotator and a plunger rod. The internal portion includes longitudinally spaced elements corresponding to the plurality of dose settings. The elements interface with the plunger rod and limit the plunger rod's maximum proximal-to-distal travel.

The rotator is an elongated tube which is rotatable within the main housing. The rotator is rotatably and linearly engaged with the needle shield via a cam and follower arrangement. The rotator is also rotatably engaged with the plunger rod. The rotator can be rotated via the cam and follower arrangement and linear motion of the needle shield. This in turn rotates the plunger rod during a compression stroke of the needle shield.

The plunger rod is housed within the main housing and can slide along the longitudinal axis. The plunger rod includes corresponding members which interface with the longitudinally spaced elements of the internal portion of the knob. The plunger rod can move in an incremental distal movement corresponding to one of the dosing positions, and in some embodiments to a priming position which is between the locked position and the dosing positions.

A needle assembly is permanently encased within the distal region of the main housing. The needle assembly includes a permanently attached needle with an interior end and a working end. The needle assembly and needle cannot be removed or replaced by a user without causing destruction of the device. The working end extends past the distal end of the main housing and is configured to pierce tissue and deliver FSH solution. The working end of the needle is normally enclosed by the needle shield. When the needle shield is in a most proximal position relative to the main housing, as is the case during a compression stroke, the working end of the needle will extend past the needle shield. The needle shield is opaque to block user view of the needle in the covering position.

A cartridge assembly is proximally arranged to the needle assembly. The cartridge assembly permanently encases a drug cartridge containing the sterile and preservative-free FSH solution. As the solution is preservative-free, it can only be safely used once and cannot be stored for future use. After an injection with the device, needle shield assumes the extended position and is locked in place so that the device and single-use cartridge cannot be used again. The internal end of the needle is located adjacent to a penetrable membrane of the distal side of the cartridge. The internal end of the needle is fluidly disconnected from the drug cartridge in the original locked position of the needle shield. A movable plunger is located at the proximal end of the cartridge, and is configured to interface with and be moved by the plunger rod. In some embodiments, the cartridge is slidably arranged within the cartridge assembly.

The plunger rod is initially locked in a proximal-most position via an interface with a locking element of the knob. In this position a compressed plunger rod spring maintains tension against the plunger rod, which when released results in distal actuation of the plunger rod. The plunger rod can be disengaged from the locking element via rotational movement induced by the needle shield via the rotator or by the knob.

For the later embodiment, i.e. the plunger rod can be disengaged via the knob, rotation of the knob to an unlock position, or directly to a dosing position, causes the plunger rod to disengage from the locking element, and incrementally move in a distal direction via the plunger rod spring to stop at a priming element of the knob. This action primes the needle by causing the plunger rod to distally move the cartridge into needle assembly. Accordingly, the membrane is pushed into and is punctured by the internal end of the needle to fluidly connect the FSH solution with the needle. The plunger rod also incrementally distally pushes the moveable seal a discrete distance which is only long enough to prime the needle and evacuate any air therein. For ease of use, the knob does not need to be marked with a priming position, as priming can occur by directly turning the knob to one of the seven or fewer discrete dosing positions, removing another required step for the user.

For the former embodiment, i.e. the plunger rod is disengaged via the needle shield, the needle assembly may be actuated via the cap to rotate and move proximally via a threaded arrangement when the cap is twisted off the needle shield. This movement causes the internal end of the needle to be driven towards and puncture the cartridge membrane, and thus prime the needle as described above. For this embodiment, movement of the knob does not prime the needle and only sets the maximum travel of the plunger rod, i.e., the desired dose.

In use, a user turns the knob to an unlock/prime position or directly to a desired dosing amount to set the maximum travel distance of the plunger rod, and accordingly limit the deliverable dose of FSH solution. The user also removes the cap. By these steps, the device is placed in a ready-to-use position. Priming the needle can occur via the embodiments noted above. In both embodiments, the device can be placed in a ready-to-use position in four or fewer user steps.

The user can then place the distal end of the needle shield against tissue. The main housing is then urged in a distal direction towards the relatively stationary needle shield and tissue in the compression stroke. This places the needle shield in a most proximal position relative to the main housing. The working end of the needle penetrates the tissue in this position. As the distal end of the opaque needle shield remains abutted against the tissue at all times, the needle is never visible. At or near its most proximal position the needle shield rotates the rotator, which in turn rotates and frees the plunger rod from the locking element of the knob. The plunger rod is then released and urged distally by the plunger rod spring until it is stopped at one of the seven or fewer elements of the knob corresponding to the respective dose levels. The FSH solution is then automatically discharged into the tissue over a short period of time, generally less than five seconds. In some embodiments, an audible click may be heard when the plunger rod is freed signifying the initiation of the injection. In some embodiments, a second audible click may be heard by the user when the plunger rod contacts one of the seven or fewer elements of the knob, which can provide an audible indicator that the FSH solution has been fully discharged into the tissue.

After the FSH solution has been discharged, the user pulls the device away from the tissue, which causes the main housing to move in the proximal direction via spring bias during a decompression stroke. The needle shield blocks the view of the needle at all times during the decompression stroke until the needle shield is fully extended. At full extension the needle shield can interface with a portion of the rotator, main housing, or rotator to permanently relock to the needle shield in place in the covering position. Accordingly, the single use device is rendered unusable after the decompression stroke.

I. Exemplary Construction of the FSH Delivery Device

Figure 1B:
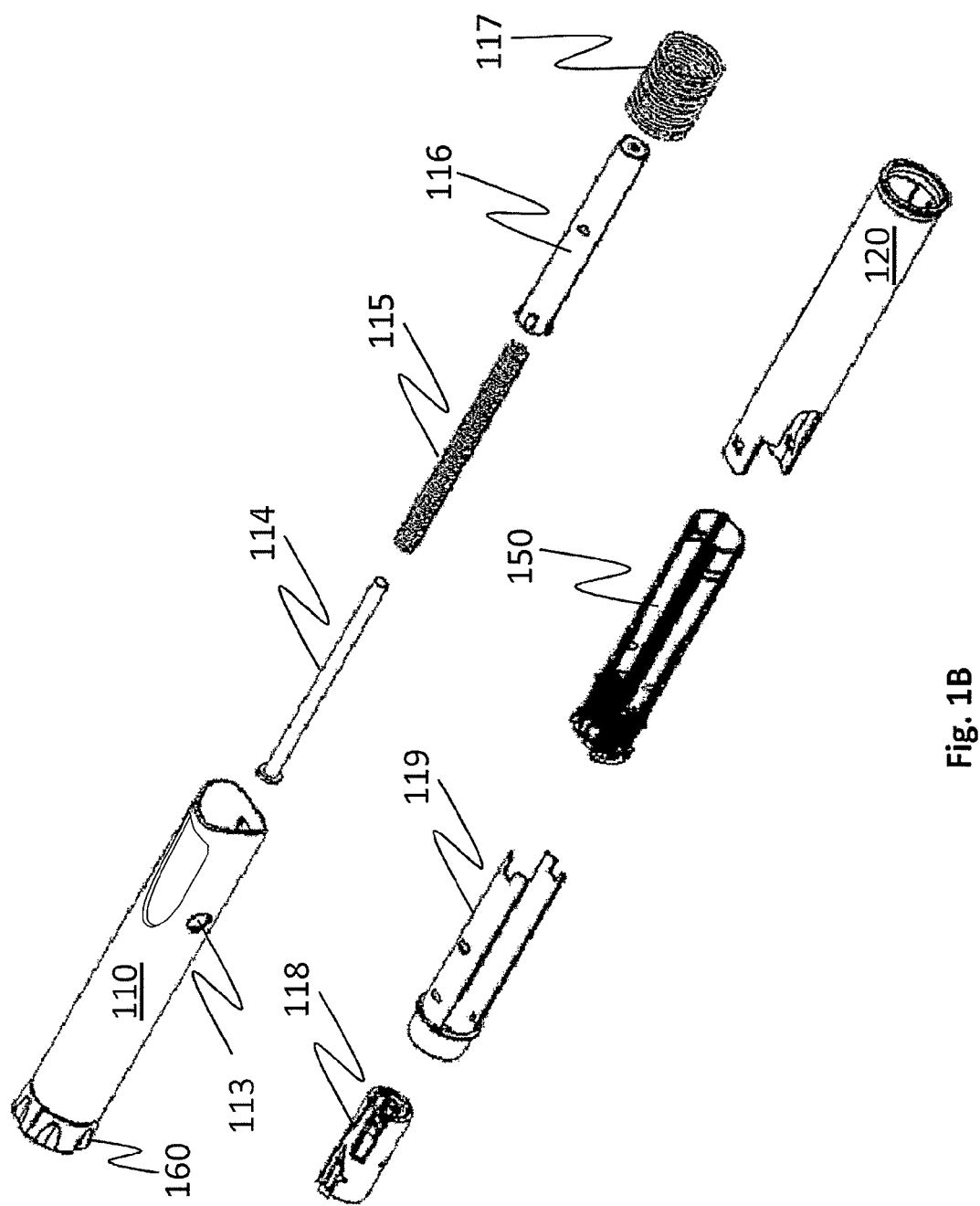
FIG. 1B illustrates an exploded view of the device of FIG. 1A.

FIG. 1A is a perspective view of a complete FSH delivery device 100 according to an embodiment of the invention and also illustrates a simplified, exploded, perspective view of the FSH injection device 100. In FIG. 1A is illustrated an initial, non-activated, state of the pre-assembled FSH injection device 100 having an outer cap 410 mounted thereon. The device 100 includes a tubular housing 110, having a distal end 111 and an opposite proximal end 112, with a needle shield 120 slidably and coaxially arranged inside the tubular housing 110, an intermediate longitudinal member 119 (see FIG. 1B) and a distal annular contact member 121. A first spring 117 (see FIG. 1B) is arranged at the distal end of the needle shield 120, between an annular ledge 202 (see FIG. 2A) of the tubular housing 110 and an annular ledge 235 (see FIG. 2B) of the intermediate longitudinal member 119 for moving the needle shield in a distal direction.

The FSH delivery device 100 includes an FSH cartridge holder 150 which is coaxially arranged within the needle shield 120 and fixedly attached to the tubular housing 110 via radial extensions 234 (see FIG. 2F) protruding through corresponding openings 113 (see FIG. 1A) in the tubular housing 110. An FSH cartridge 130 is arranged within an FSH cartridge holder 150 (see FIG. 1B). The FSH cartridge includes a moveable/slidable stopper 131, 132 (see FIG. 1A). The FSH cartridge 130 includes a membrane 133, which can be punctured by a needle. The FSH cartridge 130 is dimensioned according to the specifications of ISO 11608-3:2000 for a 1.5 ml Type A cartridge.

A rotator 118 (see FIG. 1B) having a groove, cam or follower on its inner surface and an outer protrusion on its outer surface is shown. A plunger rod 116 and a second spring 115 are arranged within the plunger rod and a plunger rod support member 114. A knob 160 is arranged at the proximal end of the tubular housing 110 and is used for activating the FSH delivery device 100, i.e. to unlock the FSH delivery device and for dose setting. The knob 160 is rotatable around a longitudinal axis extending from the proximal to the distal end of the FSH delivery device 100. The knob 160 includes seven or fewer incremented positions for setting the seven or fewer delivery doses of FSH, respectively. The knob 160 will include markings, which visually indicate these doses clearly. The rotator 118 is rotatably arranged between the cartridge holder 150 and the knob 160. The FSH delivery device 100 also includes a distally located needle assembly 140 (see FIG. 1A).

FIG. 2A shows a perspective detail view of the tubular housing 110 having the corresponding opening 113 for receiving the radial extensions 234 (see FIG. 2F) for fixedly attaching the FSH cartridge holder 150 to the tubular housing 110. FIG. 2A further illustrates a second opening 201, enabling a user to view the cartridge and FSH solution to ensure no glass breakage and that a clear particulate-free solution is safe for injection. The tubular housing 110 has an annular ledge 202, for supporting the first spring 117 (see FIG. 1B) in a pre-tensioned state, between the tubular housing 110 and the intermediate longitudinal member 119.

FIG. 2B shows the plunger rod support member 114, the second spring 115 and the plunger rod 116 in an assembled and non-tensioned state. The outer radial surface of the plunger rod 116 includes protrusions 235, adapted to co-act with an inner ledge 236 (see FIG. 3B) of the knob 160, in order to keep the plunger rod 116 in a pre-tensioned, inactivated state.

Figure 2C:
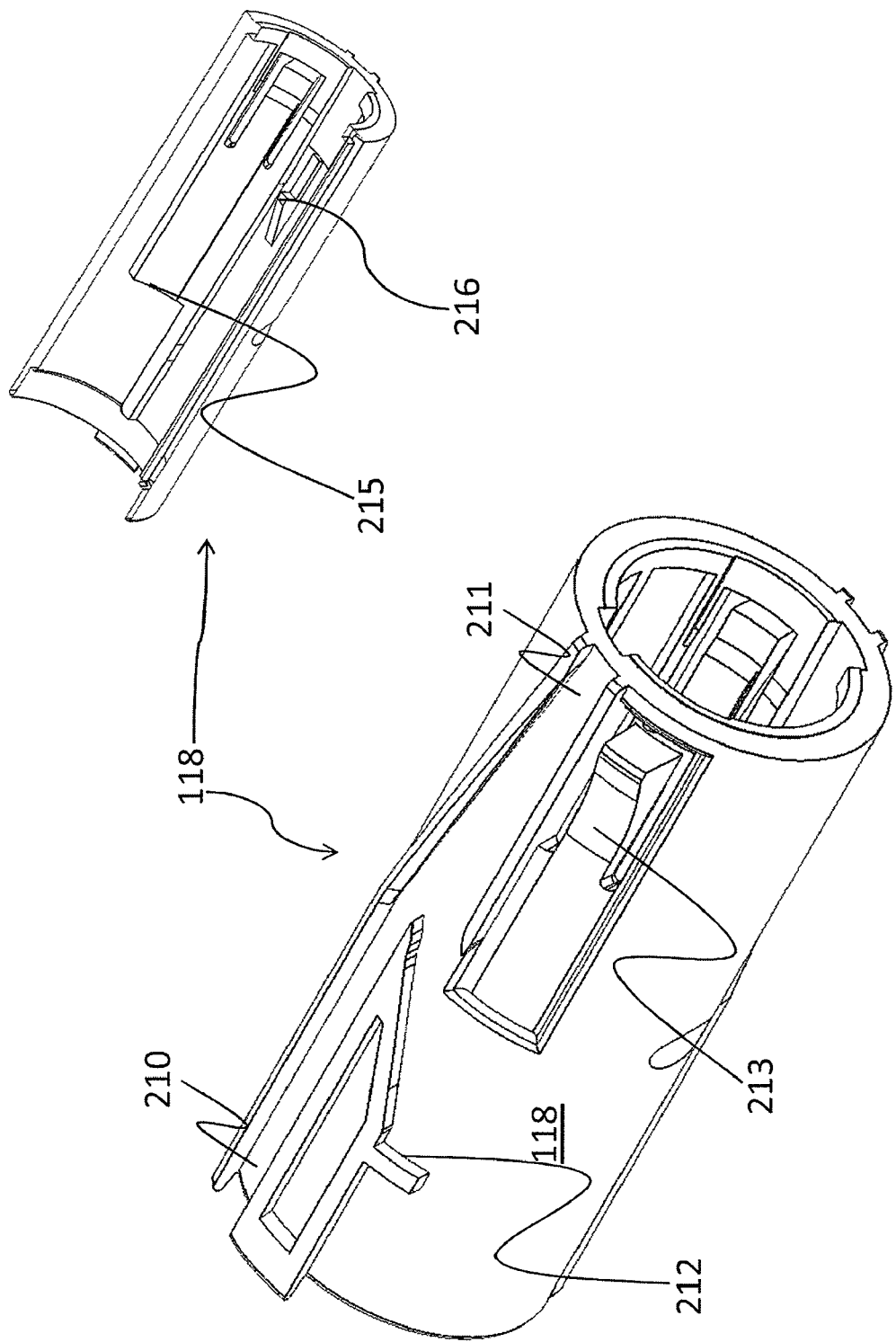
FIG. 2C is a perspective view of a rotator of the device of FIG. 1A.

FIG. 2C illustrates a detail perspective view of the rotator 118. The rotator 118 has at least one groove 210, 211, 212 on an outer surface of the rotator 118, arranged such that a radially inward extending protrusion 222 (see FIG. 2E) of the intermediate longitudinal member 119 is adapted to be guided within the at least one groove, cam or follower 210, 211, 212, forcing the rotator 118 to rotate when the intermediate longitudinal member 119 is axially moved, as a result of the axial movement of the interconnected needle shield 120. A flexible tongue 213 is arranged on the rotator 118, and is interactively connected to the intermediate longitudinal member 119 and thus also to the needle shield 120. The flexible tongue 213 is arranged to lock the second protrusion, e.g., the radially inward extending protrusion 222 of the intermediate longitudinal member 119, when the needle shield 120 has been completely extended towards the distal direction.

FIG. 2C shows also a radially inward extending protrusion 216 on the inner surface of the rotator 118 that is arranged to lock a radially outward extending flexible protrusion 203 (see FIG. 2B) on the proximal end of the plunger rod 116, when the plunger rod 116 passes through the interior of the rotator 118, i.e., when the plunger rod 116 is moved in a distal direction. FIG. 2C also illustrates in cross-sectional perspective view an inner ledge and a groove 215 of the rotator 118.

The protrusions 235 (see FIG. 2B) of the plunger rod 116 are releasably connected to the groove 215 (see FIG. 2C) of the rotator 118 for holding the plunger rod 116 (see FIG. 2B) and the second spring 115 in a pre-tensioned state, such that when the needle shield 120 is pressed against a delivery site, the rotator 118 is rotated, whereby said protrusion 235 is released from the groove 215 of the rotator 118 and the plunger rod is driven distally by the force of the second spring 115 such that the plunger rod 116 exerts a pressure on the slidable plunger 131 whereby the FSH is expelled through the needle assembly 140.

A variable dose tubular member (not shown) is fixedly connected to the knob 160 and rotatably arranged in relation to the rotator 118. The variable dose tubular member includes seven or fewer longitudinally spaced elements formed as step ledges. The plunger rod 116 includes a cooperating protrusion on its outer surface for abutting against at least one of the ledges. When the knob 160 is further manually operated for choosing a preset dose, the variable dose tubular member is also rotated such that a distance between the protrusions 235 (see FIG. 2B) of the plunger rod 116 and a step ledge on the inner surface of the variable dose member determines the size of the dose to be delivered. When the needle shield 120 is pressed against a delivery site, the rotator 118 is rotated, whereby the cooperating protrusion of the plunger rod 116 is released from the groove 215 (see FIG. 2C) of the rotator 118 and the plunger rod 116 is driven distally by the force of the second spring 115 (see FIG. 2B) such that the plunger rod 116 exerts a pressure on the slidable plunger 131,132 and the set dose of FSH is expelled through the needle assembly 140, until the protrusions 235 of the plunger rod 116 abut the step ledge on the inner surface of the variable dose member. Further exemplary dose setting mechanisms for use with the current invention are recited in U.S. Pat. No. 7,597,685, the entirety of which is incorporated for use herein for all purposes.

FIG. 2D illustrates the needle shield 120 in a perspective view. The needle shield 120 includes a recess or an opening 224 arranged to receive a corresponding protrusion 223 of the intermediate longitudinal member 119 for fixedly attaching the intermediate longitudinal member 119 to the needle shield 120. The needle shield 120 further includes an annular contact member 121 arranged for pressing against the skin of a patient.

FIG. 2E is a perspective view of the intermediate longitudinal member 119. The intermediate longitudinal member 119 includes a protrusion 221 adapted to co-act with a corresponding protrusion 301 (see FIG. 3A) of the knob 160 for holding the plunger rod 116 and the first spring 117 in a pre-tensioned state. The protrusion 221 is located on a proximal annular wall of the intermediate longitudinal member 119, and the corresponding protrusion 301 is a radially inward extending protrusion.

FIG. 2F is a perspective detail view of the FSH cartridge holder 150 showing an opening 233. There may be a corresponding opening 233 on the other side of the FSH cartridge holder 150 (not illustrated). The FSH cartridge holder 150 further includes a radial extension 234 for fixedly attaching the FSH cartridge holder 150 to the tubular housing 110 via the corresponding opening 113 (see FIG. 2A). The FSH cartridge holder 150 has an opening 233 for mating with a corresponding portion of the needle assembly (see FIG. 4A) and the FSH cartridge holder 150, and also has a predefined profile 231, 232 for fixating in a corresponding profile of the intermediate longitudinal member 119.

FIG. 2G illustrates in perspective the first spring 117 being interactively connected, in a pre-tensioned state, to an annular protrusion 202 of the tubular housing 110 and to a corresponding protrusion 225 of the intermediate longitudinal member 119.

Figure 3A:
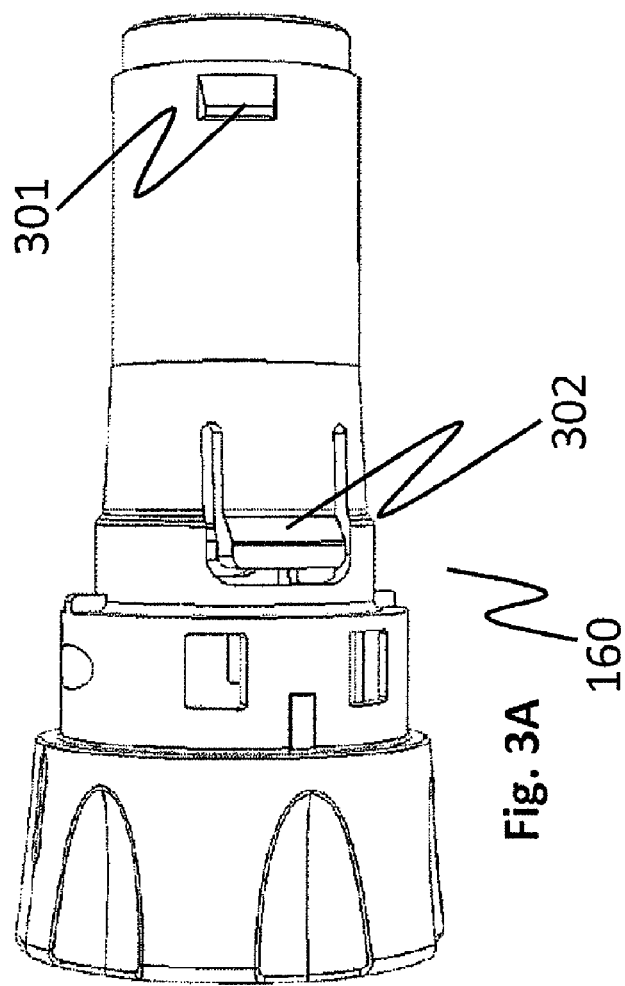
FIGS. 3A and 3B are side and cross-sectional views, respectively, of a dosing knob assembly of the device of FIG. 1A.

FIG. 3A illustrates a side view of the knob 160. The knob 160 has a flexible tongue 302 for attaching the knob 160 to a corresponding groove of the distal end of the tubular housing 110. The knob 160 further comprises a protrusion 301 for interactively connecting the knob 160 to a corresponding protrusion 221 (see FIG. 2E) of the intermediate longitudinal member 119.

Figure 3B:
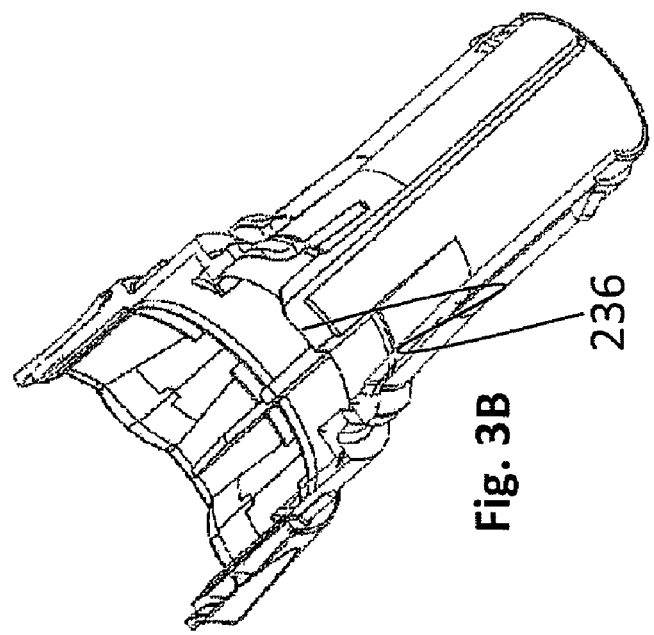

FIG. 3B is a cross-sectional perspective view of the knob 160 showing the groove as a ledge 236 arranged to co-act with the corresponding protrusions 235 (see FIG. 2B) of the plunger rod 116 in order to keep the plunger rod 116 assembly in a pre-tensioned state.

II. Exemplary Self-Priming Needle Assembly

Figure 4A:
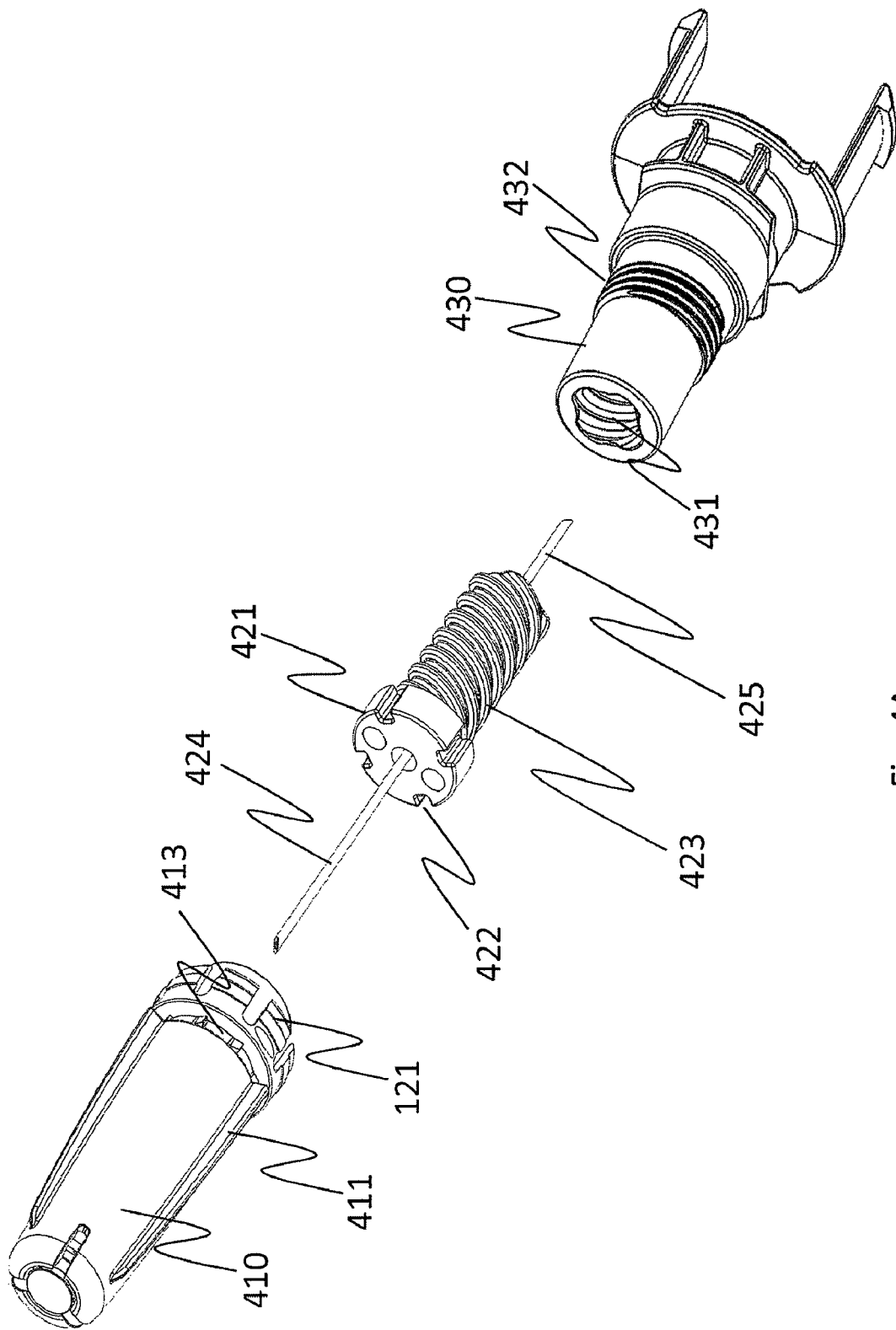
FIGS. 4A and 4B are exploded-perspective and distal-perspective views of a cap/priming assembly of the device of FIG. 1A.

FIG. 4A shows a perspective view of the needle assembly 140. A retainer member 430 is fixedly connected to the FSH cartridge holder 150. A hub 421 holds a needle having a working end 424 and an internal end 425. The hub includes threads 423 adapted to be interactively connected to corresponding threads 431 of the retainer member 430. An inner cap 416 (see FIG. 4B) is interactively connected to the hub 421 and to the retainer member 430. An outer cap 410 is coaxially arranged to the inner cap 416, wherein said outer cap 410 is rotatable in relation to said inner cap 416 when the plunger rod 116 and the first spring 117 are in the pre-tensioned state. A cap interlocking member 413 is axially slidable, but rotationally locked to the inner cap 416 and arranged abutting the annular contact member 121 (see FIG. 1A). The cap interlocking member 413 is also arranged to interact with the outer cap 410 when the actuator plunger rod 116 and the first spring 117 are released from its pre-tensioned state.

The hub 421 also includes radial recesses 422 in the distal end of the hub 421. The radial recesses 422 are interactively connected to corresponding radially inward extensions 415 (see FIG. 4B), of the inner cap 416. The hub 421 is coaxially movable within the retainer member 430. Upon movement of the hub 421 in the proximal direction, the internal end 425 will penetrate the membrane 133 (see FIG. 1A). The cap interlocking member 413 is an intermediate annular member, having a protrusion adapted to engage with a corresponding annular protrusion 417 on the inner sheath of the outer cap 410, enabling rotation of the outer cap 410.

Figure 4B:
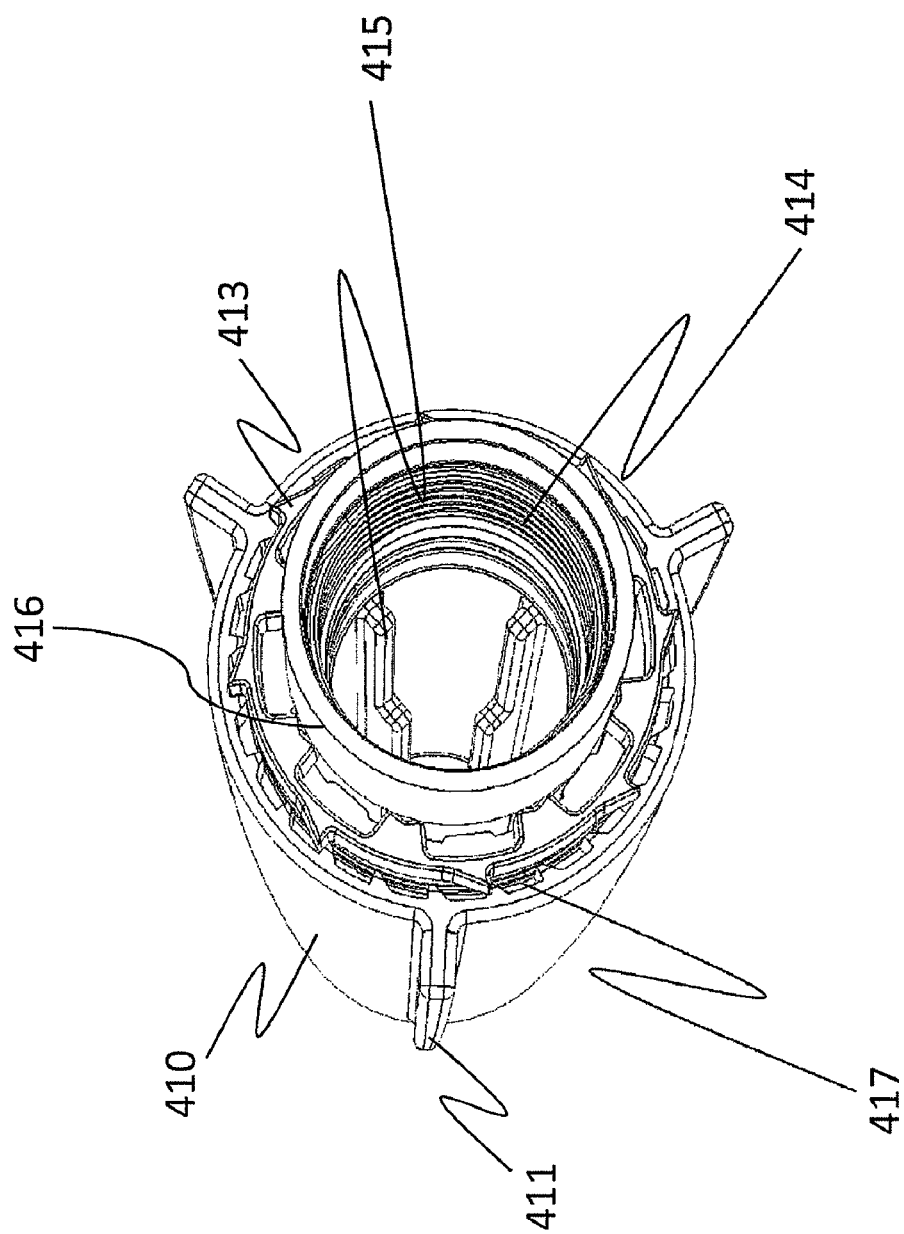

FIG. 4B is a perspective view of the outer cap 410 seen from its proximate end. The outer cap 410 comprises on its outer surface one or many radially outward extending turning members 411 provided for enabling a user-friendly and easy grip of the outer cap 410 when turning off the outer cap 410. As an alternative, the outer cap 410 may be provided with smaller inward grooves to enable an easy grip or an increased cross-sectional diameter in the section of the outer cap 410 arranged distally to the needle shield 120 when the cap 410 is attached to the FSH delivery device 100. Also in FIG. 4B is seen the inner cap 416 having internal threads 414 interactively connected to corresponding internal threads 432 of the retainer member 430 (see FIG. 4A). The internal threads 414 are arranged at the inner surface of an outer sheath of the inner cap 416 having a circular cylindrical shape. It is, however, to be noticed that the threads 414, 432 between the inner side of the inner cap 416 and the outer surface of the retainer member 430 have a different direction of the pitch than the threads 423, 431 between the hub 421 and the inner surface of the retainer member 431.

When the user then starts to turn the outer cap 410, when engaged to the inner cap by the cap interlocking member, the hub 421 screws into the retainer member 430 whereby the internal end 425 of the injection needle penetrates the membrane 133 of the FSH cartridge 130 and, due to the different direction of the pitch, the inner cap 416 is screwed off and thereby the outer cap and the inner cap may be removed. The hub 421 may apply enough force against the FSH cartridge 130 such that the needle becomes primed with FSH solution during removal of the cap. Preferably, the pitches of the threads are chosen such that there is a major longitudinal movement of the hub 421 in the proximate direction for a small turning angle in order to prevent as much as possible turning or "drilling" of the internal end 425 of the injection needle in the membrane 133. At the same time the pitch of the threads between the outer cap 410 and the retainer member 430 is preferably chosen such that the user only needs to turn the outer cap 410 about half a turn in order to perform the operation, so as to avoid having to change grip in order to finish the operation.

In FIG. 4B is further illustrated the cap interlocking member 413 for locking the outer cap 410 to the inner cap 416. When the cap interlocking member 413 is in its unlocked position, the outer cap 410 is rotatably spinning in relation to said inner cap; i.e., it is impossible to remove the outer cap 410. Thus it is not possible to use the FSH delivery device 100 when the cap interlocking member 413 is in its unlocked position. When the knob 160 is rotated, a protrusion 221 on the outer annular wall of the intermediate longitudinal member 119 is released from the cooperating protrusion 301 of the knob 160 (see FIG. 7A and FIG. 7B) and the needle shield 120 is forced in the distal direction, by the force exerted by the first spring 117, whereby the annular contact member 121 which is in contact with the cap interlocking member 413 pushes the cap interlocking member 413 distally, such that the outer cap is locked to the inner cap, which is a locked position of the cap interlocking member 413 (see FIG. 6A to FIG. 6C). The device 100 can also make use of the needle priming mechanism illustrated in international publication WO/2009/150078A1, the entirety of which is incorporated by reference herein for all purposes.

Figure 5:
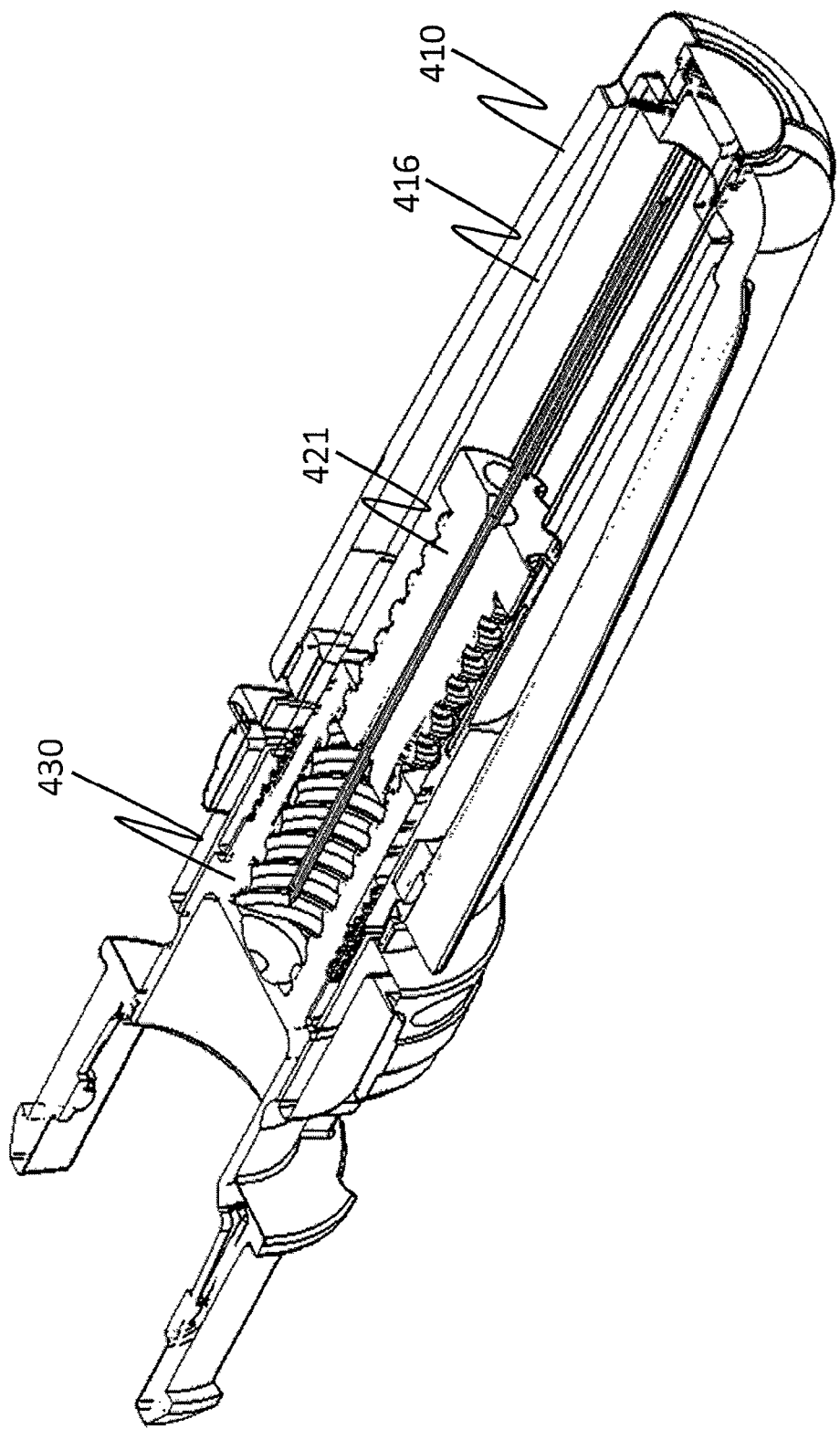
FIG. 5 is a cross-sectional view of the cap/priming assembly of FIG. 4A.

III. Exemplary Operational Modes:

III (a). Priming Via Cap Removal:

FIG. 5 is a cross-sectional perspective view of the delivery assembly showing the retainer member 430 which is fixedly connected to the FSH cartridge holder 150, the outer cap 410, the inner cap 416 and the hub 421.

FIG. 6A illustrates a cross-sectional side view of the outer cap 410 and the retainer member 430 assembly in an initial mode, where the cap interlocking member 413 is in an unlocked position.

FIG. 6B illustrates the same cross-sectional side view of the outer cap 410 and the retainer member 430 assembly where the cap interlocking member 413 is pushed axially in a proximal direction by the needle shield 120 to a locked position.

FIG. 6C again illustrates the same cross-sectional side view of the outer cap 410 and retainer member 430 assembly in a "primed" mode where the cap interlocking member 413 remains in the locked position and where outer cap 410 is being removed, causing the hub 421 to move axially in a proximal direction, forcing the distal needle end 425 to penetrate the membrane 133 of the FSH cartridge 130 and prime the needle.

III (b). Unlocking the Needle Shield:

FIG. 7A is a perspective illustration of the knob 160 in an initial, inactivated state, interactively connected to the intermediate longitudinal member 119. In the initial state the protrusion of the intermediate longitudinal member 119 is engaged to the corresponding protrusion of the knob 160.

FIG. 7B is a perspective illustration of the knob 160 in a second, activated state, interactively connected to the intermediate longitudinal member 119. The knob 160 has been turned to unlock the device. The knob 160 may include a visual marking and/or indent which indicates to the user that the device is unlocked. Unlocking the device may also occur by turning the knob 160, which may be directly turned to a dose setting as described herein. In the unlocked state, the protrusion of the intermediate longitudinal member 119 is released from its engagement to the corresponding protrusion of the knob 160, and in turn allows the needle shield 120 to be moved in a proximate direction upon application of force to the housing 110. The device is now ready to use.

III (c). Using the Device:

FIGS. 8A-8C illustrate, in perspective, the FSH delivery device 100 from its activated state, shown in FIG. 8A, wherein the internal end 425 of the needle (see also FIG. 4A) has penetrated the membrane 133 (FIG. 1A) and the FSH delivery device 100 is in a ready-to-use state, via FIG. 8B, wherein is illustrated the actual injection state, showing a distal needle end 424 ready to expel the FSH solution, and finally in FIG. 8C is shown a locked state of the FSH delivery device 100; i.e. injection has been made.

When the FSH delivery device 100 is ready for use and the user is about to make an injection he/she presses the distal end, i.e. the annular contact member 121, against the user's tissue, i.e. skin, to cause the compression stroke of the device. The housing 110 is then moved in a distal direction in relation to the relatively stationary needle shield 120 held against the tissue, and the proximal needle end 425 penetrates the skin. When the needle shield 120 is about to be placed in its most proximal position, in relation to the tubular housing 110, the injection is made; i.e., when the needle shield 120 passes by a predetermined injection position, close to its most proximal position, the initiation of the injection state is achieved. The device 100 may emit a first audible click caused by interaction between the rotator 118 and the plunger rod 116 to indicate that the injection state has begun. The device 100 may emit a second audible click caused by interaction of the plunger rod 116 with a dose stopping/setting element, which indicates to the user that the injection is complete. The injection period may take fewer than five seconds to complete.

It should be understood that the needle shield 120 is opaque to block the view of the needle before, during and after the compression stroke of the device for injection of the FSH solution into the patient. Accordingly, needle anxiety can be alleviated by preventing the user from viewing the needle before and after the compression stroke, and accordingly before and after the decompression stroke to the final locked and unusable state of the device.

This penetration and injection state is shown in FIGS. 8A-8C. When the injection is completed, the user removes the FSH delivery device 100 from the skin, thereby allowing a decompression stroke of the needle shield 120 (see FIG. 8C). During the decompression stroke the housing 110 moves in a proximal direction in relation to the needle shield 120 by a force exerted by the first spring 117 and to finally reach its final state, i.e., the locked state. In the locked state, the needle shield 120 once more is in its most distal position as illustrated by FIG. 8C. In this state, the needle shield 120 fully protects the working end 424 of the needle, and the needle shield 120 is also locked in that position, in order to prevent unintentional availability of the working end 424. Thus, for activating the FSH delivery device 100 a user has to press the annular contact member 121 against the skin, which will release the plunger rod 116 in a distal direction in relation to the tubular housing 110, exerted by force of the second spring 115. The plunger rod 116 will thus force the movable plunger 131, 132 to also move in a distal direction in relation to the tubular housing 110, causing the FSH solution to be expelled from the needle.

Figure 9B:
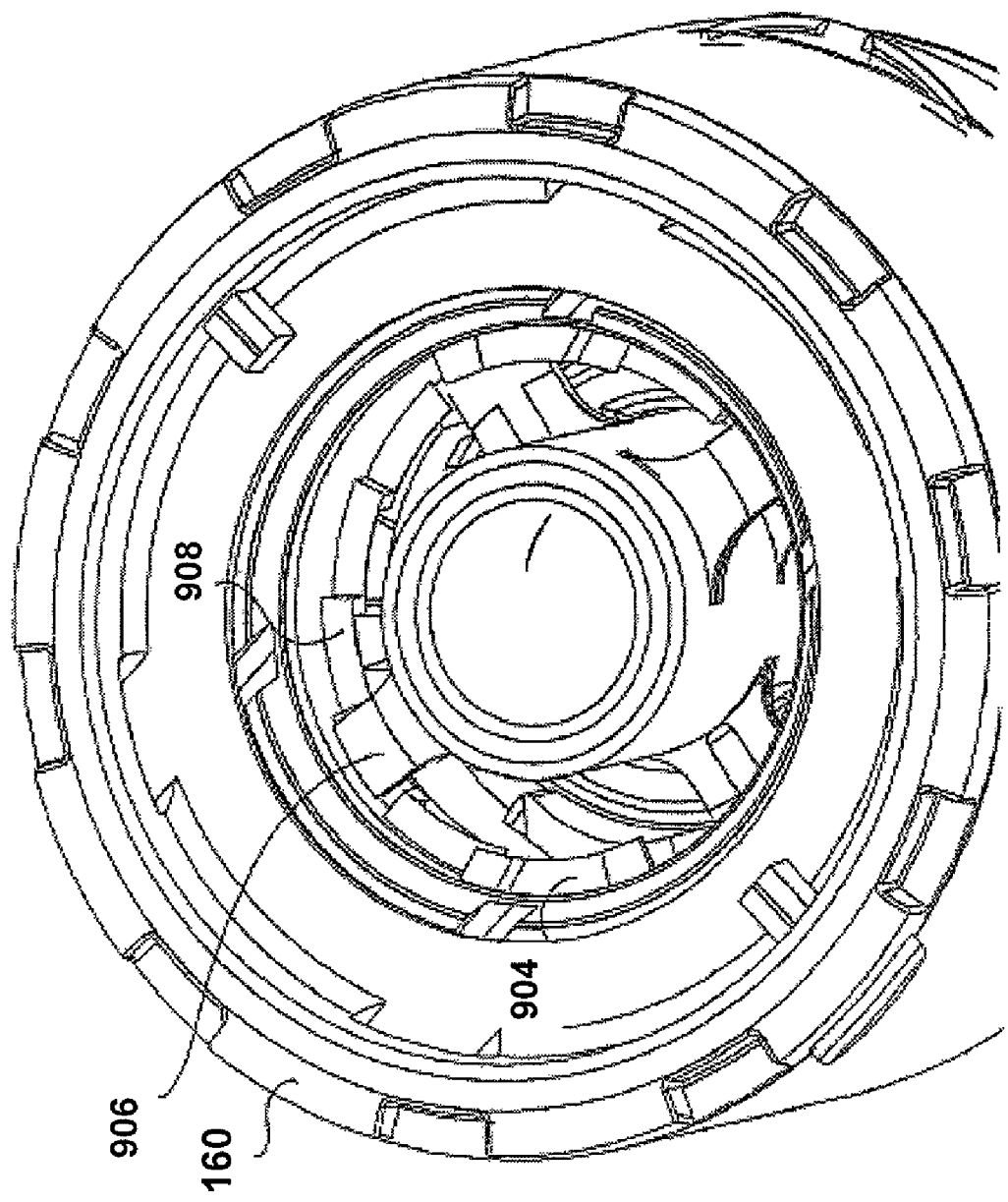
FIGS. 9B and 9C are perspective views of a dosing setting assembly for use with the devices of FIGS. 1A and 9A.
Figure 9C:
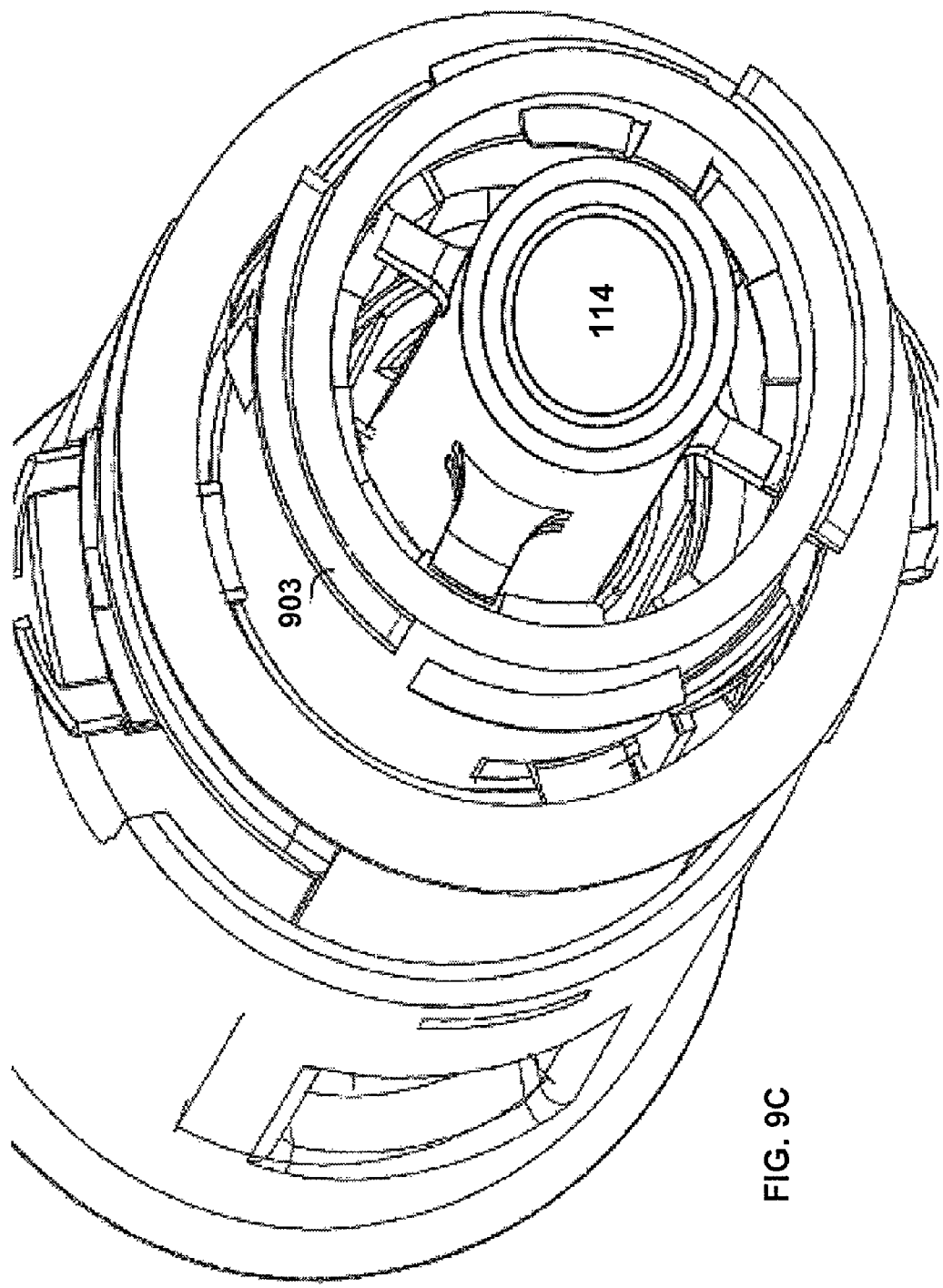

IV. Exemplary Variable Dosing and Priming Mechanism:

FIGS. 9A to 9C show a dose setting feature, according to an embodiment of the invention. This feature can be used to provide injectors for different doses of FSH solution.

The intermediate longitudinal member 119 is arranged between the dose setting knob 160 and the rotator 126 as shown in FIG. 9B. The intermediate longitudinal member 119 is rotationally locked to the dose setting knob 160 by outwardly extending, oppositely arranged claws 903 (see FIG. 9C), between which are found corresponding inwardly extending claws on the dose setting knob 160. The plunger rod support member 114 is held in an initial position by a set of oppositely arranged outwardly extending knobs 906 on the intermediate longitudinal member 119 abutting a first series of longitudinally spaced elements, which may be ledges 904 arranged on the inner surface of the dose setting knob 160.

Turning of the knob 160 to the priming position, or directly to a desired dose position, causes the knobs 906 to slide off the ledges 904. In some embodiments, a priming position is not indicated on the knob, and turning the knob 906 directly to a desired setting position will cause the knobs 906 to slide off the ledges 904. The force of the second spring 115 pushes the plunger rod support member 114 forward to an incremental priming position, expelling any prevailing air in the cartridge 130.

In this embodiment, the cartridge is slidable with regards to a stationary needle assembly 910, as shown in FIG. 9A. The device in this embodiment also includes a distally located needle cap (not shown) which is removed before use, although the needle cap does not rotationally engage the needle assembly for the purpose of priming. Accordingly, the plunger rod is configured to move the cartridge 130 into the needle assembly 910 to first puncture the membrane 133 during priming. The plunger rod continues to push the movable plunger 131, 132 to prime the cartridge 130. The movement is stopped when a second set of knobs (not shown) of the plunger rod support member 114 abuts a second set of ledges arranged on the inner surface of the rotator 126.

The dose setting knob is now free to be turned to set a certain dose. For this purpose the inner surface of the tubular member 902 is arranged with a second series of longitudinally spaced elements, i.e. ledges 908 (see FIG. 9B), at certain distances from the proximal end of the injector, forming a set of descending ledges. Each ledge corresponds to a certain dose to be delivered by limiting the maximum travel of the plunger rod support member 114. Generally, seven or fewer ledges are provided for seven or fewer respective discrete doses of FSH solution. The incremental turning of the knob is indicated by appropriate symbols or signs to show the user which dose is set. As shown in FIG. 9A, the distance X corresponds to the length of the plunger to travel during injection, and thus corresponding to the delivered dose.

The device is now ready for injection. When pressing the device against the injection site and penetrating the skin, the guide knobs of the intermediate longitudinal member 119 rotate the rotator 126 as described above, whereby the outwardly extending knobs 906 of the plunger slip off the second set of ledges 149. This causes the plunger rod 116 to move forward, causing an injection until the outwardly extending knobs 906 abut one of the descending ledges 908 that is set for a certain dose. The outwardly extending knobs 906 can strike one of the descending ledges with enough force to cause an audible click to be heard by the user to indicate that the desired dose has been delivered. Additionally, the maximum possible dose can be delivered in five seconds or less, i.e. within five seconds after the needle shield is placed into the injecting position.

When the injection is finished the user removes the device and the needle shield 120 will permanently lock after the decompression stroke of the needle shield 120, and thus be rendered unusable. Further exemplary dose setting mechanisms for use with the current invention are recited in U.S. Pat. No. 7,597,685.

V. Exemplary FSH Delivery Devices

FIGS. 10A-10F show various views of a styled FSH delivery device 1000, according to an embodiment of the invention. The FSH delivery device 1000 functions and is constructed according to the various embodiments disclosed herein, and accordingly includes the internal aspects (such as an elongated rotator, plunger rod, needle assembly, cartridge holder, and FSH cartridge) that have been well described above with respect to all embodiments of the FSH delivery device 100.

The FSH delivery device 1000 includes a tubular housing 1010. The tubular housing 1010 includes a window 1012 to allow inspection of an FSH cartridge within the tubular housing 1010. The tubular housing 1010 is functionally coupled to a dose knob 1015, which can be turned from a locked position to a desired dosing position, as shown in FIG. 10F.

A removable needle cap 1020 is removably coupled to the tubular housing 1010. Removal of the needle cap 1020 via rotation, causes an internal needle assembly (not shown) to prime the FSH cartridge and extend a needle shield 1025. In an alternative embodiment, priming is triggered via the dosing knob 1015, while removal of the cap 1020 causes the needle shield to extend. Such priming mechanisms are well described above.

In use, a user turns the dosing knob 1015 to a prescribed dose by turning the knob 1015, from the locked position shown in FIG. 10A, until a desired dose aligns with an indicator on the knob 1015. The user also removes the needle cap 1020 to cause the needle shield 1025 to extend and shield a fixed needle from both user view and accidental contact, before or after setting the dose.

The user then applies a distal most edge of needle shield 1025 to a portion of skin of the user (or that of another person) and pushes the tubular housing 1010 towards the skin. This motion causes the needle shield 1025 to partially retract into the tubular housing 1010 such that the distal most edge of the needle shield 1025 is proximal to the tip of the fixed needle. The fixed needle thus punctures the skin and delivers FSH solution via internal action of the plunger rod against the FSH cartridge, which is described herein.

During this step, the user maintains the tubular housing 1010 in position against the skin for a moment (e.g., five seconds) to completely deliver the chosen dose. The user can also confirm that the FSH solution is being, or has been delivered, by observing depletion of the FSH solution through the window 1012. Removal of the FSH delivery device 1000 from the portion of skin causes the needle shield 1025 to simultaneously extend and re-shield the fixed needle, thus preventing the user from ever viewing the fixed needle. In some embodiments the needle shield 1025 will lock into the extended position and thus be rendered immoveable to prevent reuse. Accordingly, the prescribed dose of FSH is deliverable using the FSH delivery device 1000 in four or fewer steps.

FIGS. 11A-11F show various views of another styled FSH delivery device 1100, according to an embodiment of the invention. The FSH delivery device 1100 functions and is constructed according to the various embodiments disclosed herein, and accordingly includes the internal aspects (such as an elongated rotator, plunger rod, needle assembly, cartridge holder, and FSH cartridge) that have been well described above with respect to all embodiments of the FSH delivery device 100.

The FSH delivery device 1100 includes a rectangular housing 1110. The rectangular housing 1110 is functionally equivalent to the tubular housing 1010 described above. The rectangular housing 1110 includes a window 1112 to allow inspection of an FSH cartridge within the tubular housing 1110. The rectangular housing 1110 is also functionally coupled to a dose knob 1115, which can be turned from a locked position (as shown in FIG. 10A) to a desired dosing position (as shown in FIGS. 11C and 11F). The knob 1115 is functionally coupled to an internal dosing barrel 1117, which rotates with the knob 1115 to show different doses made available by the FSH delivery device 1100.

A removable needle cap 1120 is removably coupled to the rectangular housing 1110. Removal of the needle cap 1120 via rotation, causes an internal needle assembly (not shown) to prime the FSH cartridge and extend a needle shield 1125. In an alternative embodiment, priming is triggered via the dosing knob 1115, while removal of the cap 1120 causes the needle shield 1125 to extend. Such priming mechanisms are well described herein.

Figure 11A:
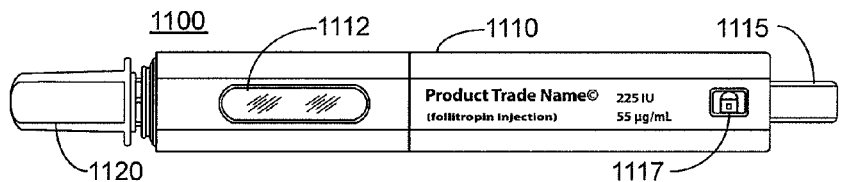
FIGS. 11A and 11B are different side views of a rectangular FSH delivery device, according to an embodiment of the invention.
Figure 11B:
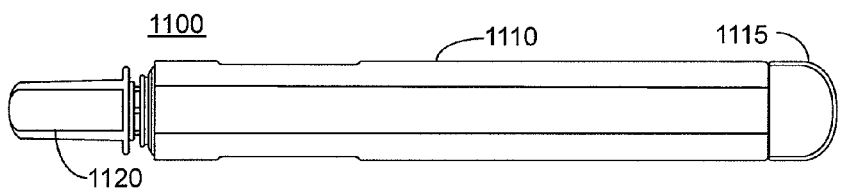
Figure 11C:
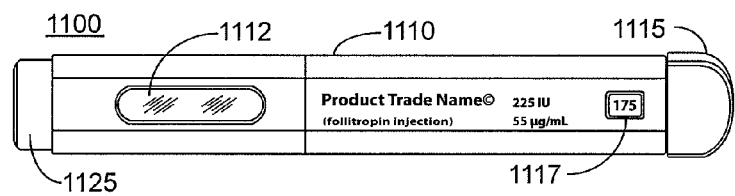
FIG. 11C is a side view the FSH delivery device of FIG. 11A in a mode of operation.
Figure 11D:
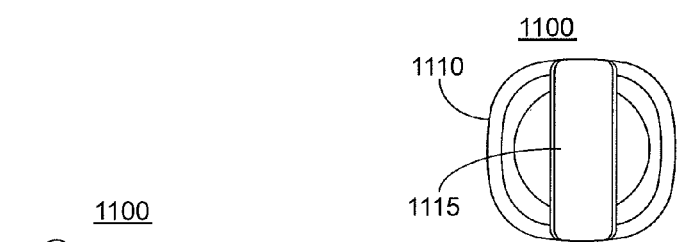
FIGS. 11D and 11E are distal and proximal views, respectively, of the FSH delivery device of FIG. 11A.
Figure 11E:
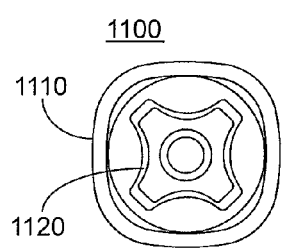
Figure 11F:
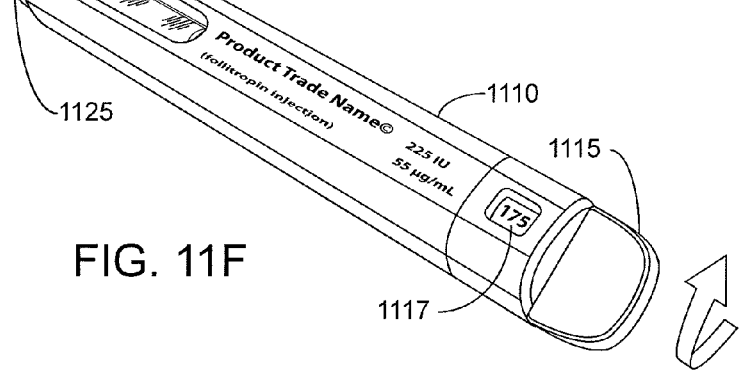
FIG. 11F is a perspective view the FSH delivery device of FIG. 11A in a mode of operation.

In use, a user turns the dosing knob 1115 to a prescribed dose by turning the knob 1115, from the locked position shown in FIG. 11A, until a desired dose labeled on the internal dosing barrel 1117 is made visible through the rectangular housing 1110, as shown in FIGS. 11C and 11F. The user also removes the needle cap 1120 to cause the needle shield 1125 to extend and shield a fixed needle from both user view and accidental contact, before or after setting the dose.

The user then applies a distal most edge of needle shield 1125 to a portion of skin of the user (or that of another person) and pushes the rectangular housing 1110 towards the skin. This motion causes the needle shield 1125 to partially retract into the rectangular housing 1110 such that the distal most edge of the needle shield 1125 is proximal to the tip of the fixed needle. The fixed needle thus punctures the skin and delivers FSH solution via internal action of the plunger rod against the FSH cartridge, which is described herein.

During this step, the user maintains the rectangular housing 1100 in position against the skin for a moment (e.g., five seconds) to completely deliver the chosen dose. The user can also confirm that the FSH solution is being, or has been delivered, by observing depletion of the FSH solution through the window 1112. Removal of the FSH delivery device 1100 from the portion of skin causes the needle shield 1125 to simultaneously extend and re-shield the fixed needle, thus preventing the user from ever viewing the fixed needle. In some embodiments the needle shield 1125 will lock into the extended position and thus be rendered immoveable to prevent reuse. Accordingly, the prescribed dose of FSH is deliverable using FSH delivery device 1100 in four or fewer steps.

The above description is illustrative and is not restrictive. Many variations of the invention will become apparent to those skilled in the art upon review of the disclosure. The scope of the invention should therefore be determined not with reference to the above description, but instead should be determined with reference to the pending claims along with their full scope or equivalents.

What is claimed is:

1. A single-use device for self-delivery of follicle stimulating hormone solution, the device comprising:
    an elongated main housing with distal and proximal portions arranged along a longitudinal axis;
    an elongated rotator being connected to the proximal portion of the main housing and rotatable about the longitudinal axis with respect to the main housing;
    a knob extending from the proximal portion of the housing and being rotatable with respect to the main housing between a lock position and seven or fewer discrete dosing positions for setting variable dose delivery of follicle stimulating hormone (FSH) solution, the knob having longitudinally spaced elements respectively corresponding to the lock position and the seven or fewer discrete dosing positions;
    a plunger rod rotatably engaged to a portion of the rotator and longitudinally spring biased, the plunger rod being rotatably locked to the knob in the locked position on the element corresponding to the lock position, the plunger rod being incrementally movable along the longitudinal axis between the element corresponding to the lock position and one of the elements of the seven or fewer discrete dosing positions;
    a permanently encased needle assembly having a permanently attached needle, the needle having an internal end and a working end;
    a cartridge holder proximately attached to the needle assembly, the cartridge holder holding an elongated drug cartridge containing the FSH solution, the FSH solution being sterile and preservative free to allow only a single use of the device, the drug cartridge being permanently encased within the cartridge retainer and having a penetrable membrane adjacent the internal end of the needle and a movable plunger adjacent to the plunger rod, the drug cartridge being fluidly disconnected from the internal end of the needle when the knob is in the locked position;
    a needle shield movable with respect to the main housing along the longitudinal axis between a covering position that is distal to the working end of the needle and an injecting position that is proximal to the working end of the needle, the needle shield being spring biased to be normally placed in the covering position and being opaque to substantially block user view of the working end of the needle in the covering position, the needle shield having a cam or follower which rotatably and longitudinally interfaces with a respective follower or cam of the rotator during a compression stroke of the needle shield from the covering position to the injecting position; and
    a removable cap positioned to cover the working end of the needle,
    wherein the needle assembly or the drug cartridge is movable along the longitudinal axis to a priming position via engagement with the cap or plunger rod, respectively, to cause the internal end of the needle to penetrate the membrane and fluidly connect with the drug cartridge to prime the needle with the FSH solution,
    wherein during the compression stroke the needle shield moves to the injecting position and rotates the rotator to rotatably engage the plunger rod and cause the plunger rod to move to one of the elements of the seven or fewer discrete dosing positions and compress the movable plunger to deliver a corresponding discrete dose amount of FSH solution from the working end of the needle,
    wherein the user steps needed to place the unpackaged device from the lock position to a ready-to-use position are four or fewer.

2. The device of claim 1, wherein the knob is rotatable with respect to the main housing between the lock position and a prime position.

3. The device of claim 2, wherein the knob includes a longitudinally spaced priming element corresponding to the prime position, the priming element being located between the lock position and the seven or fewer discrete dosing positions.

4. The device of claim 3, wherein rotating the knob to or past the prime position rotates the plunger rod from the lock position and incrementally moves the plunger rod along the longitudinal axis between the element corresponding to the lock position and the priming element.

5. The device of claim 4, wherein the plunger rod is incrementally moved along the longitudinal axis to move the drug cartridge into the needle assembly and cause the membrane to be punctured by the working end of the needle and prime the needle with the FSH solution.

6. The device of claim 5, wherein the user steps needed to place the unpackaged device from the lock position to the ready-to-use position consist of:
    priming the needle with the FSH solution by rotating the knob from the lock position, past the priming position, to one of the seven or fewer discrete dosing positions; and
    removing the needle cap.

7. The device of claim 6, wherein the rotator knob is visually marked with discrete positions indicating the seven or fewer discrete dosing positions.

8. The device of claim 7, wherein the priming position is not marked on the knob.

9. The device of claim 6, wherein distal movement of the main housing with respect to the needle shield held against relatively immobile tissue causes the compression stroke.

10. The device of claim 1, wherein the needle assembly includes a hub attached to the needle, the hub being threadably engaged with a retainer member of the needle assembly.

11. The device of claim 10, wherein the removable cap is rotatably engaged with the retainer member, and wherein rotation of the removable cap disengages the removable cap from the device and also moves the hub in a proximate direction with respect to the retainer member and accordingly causes the membrane to be punctured by the working end of the needle and prime the needle with the FSH solution.

12. The device of claim 11, wherein the user steps needed to place the unpackaged device from the lock position to the ready-to-use position consist of:
   priming the needle with the FSH solution by removing the needle cap; and
   rotating the knob from the lock position to one of the seven or fewer discrete dosing positions.

13. The device of claim 12, wherein distal movement of the main housing with respect to the needle shield held against relatively immobile tissue causes the compression stroke.

14. The device of claim 1, wherein the drug cartridge is 1.5 ml in volume.

15. The device of claim 14, wherein the plunger rod is configured to deliver a maximum dose of the FSH solution within five seconds after the needle shield is placed in the injecting position.

16. The device of claim 1, wherein the needle shield includes a locking element which locks to the rotator or main housing during a decompression stroke of the needle shield from the injecting position to a recovering position to recover the working end of the needle, and wherein the needle shield is immovable with respect to the main housing after moving to the recovering position.

17. The device of claim 1, wherein the plunger rod contacts one of the elements of the seven or fewer discrete dosing positions with enough force to cause an audible click to be heard by the user.

18. The device of claim 1, wherein the FSH solution does not contain benzyl alcohol or m-cresol.

19. The device of claim 1, wherein the needle shield completely blocks the user's view of the working end of the needle in the covering position when the distal end of the needle shield is held against the user's tissue before and after the compression stroke occurs.

* * * * *